United States Patent
Reardon

(10) Patent No.: US 9,493,806 B2
(45) Date of Patent: Nov. 15, 2016

(54) ENZYMATIC BIOSENSING SYSTEMS

(75) Inventor: Kenneth F. Reardon, Fort Collins, CO (US)

(73) Assignee: COLORADO STATE UNIVERSITY RESEARCH FOUNDATION, Fort Collins, CO (US)

(*) Notice: Subject to any disclaimer, the term of this patent is extended or adjusted under 35 U.S.C. 154(b) by 816 days.

(21) Appl. No.: 13/562,592

(22) Filed: Jul. 31, 2012

(65) Prior Publication Data
US 2014/0235501 A1 Aug. 21, 2014

Related U.S. Application Data

(63) Continuation-in-part of application No. 12/100,308, filed on Apr. 9, 2008, which is a continuation-in-part of application No. 10/478,822, filed as application No. PCT/US02/17407 on Jun. 1, 2002, now Pat. No. 7,381,538.

(60) Provisional application No. 60/922,496, filed on Apr. 9, 2007, provisional application No. 61/024,453, filed on Jan. 29, 2008, provisional application No. 60/295,211, filed on Jun. 1, 2001.

(51) Int. Cl.
*C12Q 1/34* (2006.01)
*C12Q 1/527* (2006.01)
*C12Q 1/00* (2006.01)

(52) U.S. Cl.
CPC .............. *C12Q 1/005* (2013.01); *C12Q 1/002* (2013.01); *G01N 2333/90241* (2013.01); *G01N 2333/90245* (2013.01); *G01N 2333/914* (2013.01); *G01N 2333/988* (2013.01)

(58) Field of Classification Search
CPC ............................ C12Q 1/005; C12Q 1/002
USPC ............................................................ 422/72
See application file for complete search history.

(56) References Cited

U.S. PATENT DOCUMENTS

| 4,739,380 A | 4/1988 | Lauks et al. |
| 4,832,034 A | 5/1989 | Pizziconi et al. |
| 4,848,906 A | 7/1989 | Layton |

(Continued)

FOREIGN PATENT DOCUMENTS

| EP | 277699 A2 | 10/1988 |
| EP | 1078248 B1 | 2/2001 |

(Continued)

OTHER PUBLICATIONS

Peter, J. (1997). "Characteristics of a Microbial Assay for the Detection of Halogenated Hydrocarbons Using Cells of an Actinomycete-like Organism as a Biological Component." Acta Biotechnol. 17:(2). 123-130.*

(Continued)

*Primary Examiner* — Sean E Conley
*Assistant Examiner* — Jaqueline Brazin
(74) *Attorney, Agent, or Firm* — Faegre Baker Daniels LLP

(57) ABSTRACT

Biosensors and methods of producing biosensors for use in detecting one or more analytes in a solution are disclosed herein.

19 Claims, 4 Drawing Sheets

(56) References Cited

U.S. PATENT DOCUMENTS

| | | | |
|---|---|---|---|
| 4,900,423 A | 2/1990 | Iida et al. | |
| 5,140,609 A | 8/1992 | Jensen et al. | |
| 5,141,312 A * | 8/1992 | Thompson | G01J 1/04 250/227.11 |
| 5,152,758 A | 10/1992 | Kaetsu et al. | |
| 5,156,810 A | 10/1992 | Ribi | |
| 5,177,012 A | 1/1993 | Kim et al. | |
| 5,250,439 A | 10/1993 | Musho et al. | |
| 5,340,722 A * | 8/1994 | Wolfbeis | C12Q 1/005 435/14 |
| 5,462,879 A | 10/1995 | Bentsen | |
| 5,508,193 A | 4/1996 | Mandelbaum et al. | |
| 5,541,057 A | 7/1996 | Bogart et al. | |
| 5,543,317 A | 8/1996 | Shields et al. | |
| 5,580,527 A * | 12/1996 | Bell | C08F 8/42 252/301.26 |
| 5,629,214 A | 5/1997 | Crosby | |
| 5,698,083 A | 12/1997 | Glass | |
| 5,798,030 A | 8/1998 | Raguse et al. | |
| 5,837,196 A * | 11/1998 | Pinkel | C12Q 1/6825 422/400 |
| 5,837,454 A | 11/1998 | Cozzette et al. | |
| 5,853,669 A * | 12/1998 | Wolfbeis | G01N 31/221 422/408 |
| 5,866,321 A | 2/1999 | Matsue et al. | |
| 5,972,199 A * | 10/1999 | Heller | C12Q 1/005 204/403.1 |
| 5,972,638 A | 10/1999 | Burlage et al. | |
| 6,022,748 A | 2/2000 | Charych et al. | |
| 6,060,327 A | 5/2000 | Keen | |
| 6,100,080 A | 8/2000 | Johansen | |
| 6,136,979 A | 10/2000 | Hudlicky et al. | |
| 6,159,681 A | 12/2000 | Zebala | |
| 6,265,201 B1 | 7/2001 | Wackett et al. | |
| 6,271,015 B1 | 8/2001 | Gilula | |
| 6,284,522 B1 | 9/2001 | Wackett et al. | |
| 6,291,200 B1 | 9/2001 | LeJeune et al. | |
| 6,344,360 B1 | 2/2002 | Colvin et al. | |
| 6,369,299 B1 | 4/2002 | Sadowsky et al. | |
| 6,437,345 B1 | 8/2002 | Bruno-Raimondi et al. | |
| 6,576,449 B2 | 6/2003 | Clark et al. | |
| 6,592,746 B1 | 7/2003 | Schmid-Schoenbein et al. | |
| 6,766,183 B2 | 7/2004 | Walsh et al. | |
| 6,825,001 B2 | 11/2004 | Wackett et al. | |
| 6,927,246 B2 | 8/2005 | Noronha et al. | |
| 7,381,538 B2 | 6/2008 | Reardon et al. | |
| 7,595,181 B2 | 9/2009 | Gruning et al. | |
| 7,709,221 B2 | 5/2010 | Rose et al. | |
| 7,709,249 B2 | 5/2010 | Bedingham et al. | |
| 7,955,483 B2 | 6/2011 | Gu et al. | |
| 8,309,328 B1 | 11/2012 | Dhawan et al. | |
| 8,323,956 B2 | 12/2012 | Reardon et al. | |
| 8,622,900 B2 | 1/2014 | Jain et al. | |
| 8,622,901 B2 | 1/2014 | Jain et al. | |
| 2002/0168733 A1 | 11/2002 | Clark et al. | |
| 2003/0207345 A1 | 11/2003 | Arnold et al. | |
| 2004/0265811 A1 | 12/2004 | Reardon et al. | |
| 2005/0084921 A1 | 4/2005 | Cranley et al. | |
| 2005/0221276 A1 | 10/2005 | Rozakis et al. | |
| 2006/0275855 A1 | 12/2006 | Blackburn et al. | |
| 2009/0026092 A1 | 1/2009 | Reardon et al. | |
| 2009/0078886 A1 | 3/2009 | Schutzmann et al. | |
| 2009/0221014 A1 | 9/2009 | Reardon et al. | |
| 2010/0116691 A1 | 5/2010 | Papadimitrakopoulos | |
| 2013/0065224 A1 | 3/2013 | Lu et al. | |
| 2014/0154724 A1 | 6/2014 | Reardon et al. | |
| 2014/0234882 A1 | 8/2014 | Reardon et al. | |
| 2015/0232913 A1 | 8/2015 | Reardon et al. | |

FOREIGN PATENT DOCUMENTS

| | | |
|---|---|---|
| EP | 1369687 A1 | 12/2003 |
| WO | WO 93/25892 | 12/1993 |
| WO | 9958963 A1 | 11/1999 |
| WO | WO03025627 A9 | 3/2003 |
| WO | 2004060297 A2 | 7/2004 |
| WO | 2009126841 A1 | 10/2009 |

OTHER PUBLICATIONS

U.S. Appl. No. 12/100,308, Office Action mailed Apr. 6, 2015; 9 pages.

U.S. Appl. No. 14/348,426, Office Action mailed Apr. 2, 2015; 19 pages.

Carswell et al. "An Optical Oxygen Sensor Based on RUDPP Fluorescent Quenching," SPIE vol. 2705, Mar. 25, 1996, pp. 22-30.

Hollmann et al. "The First Synthetic Application of a Monooxygenase Employing Indirect Electrochemical NADH Regeneration," Chem Int. 2001. vol. 40 No. 1. pp. 169-171.

Lee et al. "Proteome Changes after Metabolic Engineering to Enhance Aerobic Mineralization of cis-1, 2-Dichloreothylene," Journal of Proteome Research, 2006, pp. 1388-1397. American Chemical Society, Web.

Mars et al. "Effect of Trichloreothylene on Competitive Behavior of Toluene-Degrading Bacteria," Applied and Environmental Microbiology, 1998, vol. 64 (1), pp. 208-215.

Neujahr, Halina, "Determination of Phenol and Catechol Concentrations with Oxygen Probes Coated with Immobilized Enzymes or Immobilized Cells," Applied Biochemistry and Biotechnology, 1982, vol. 7, pp. 107-111.

Rui et al. "Metabolic pathway engineering to enhance aerobic degradation of chlorinated ethenes and to reduce their toxicity by cloning a novel glutathione 5-transferase, an evolved toluene o-monooxygenase, and y-glutamylcysteine synthetase," Environmental Microbiology, 2004, 6(5), pp. 491-500.

Stokes et al. "An optical oxygen sensor and reaction vessel for high-pressure applications," Limnol. Ocearnogr., 1999, vol. 44(1):189-195.

Sundari et al. "Retention of enzyme activity following freeze-drying the mycelium of ectomycorrhizal isolates: part II. Enzymes acting upon carbon compounds" World Journal of Microbiology and Biotechnology, 2000, vol. 16, pp. 865-868.

Zhong, Z. "Fiber Optic Enzymatic Biosensors and Biosensor Arrays for Measurement of Chlorinated Ethenes," Dissertation, Colorado State University, (submission date Apr. 2, 2011), 158 Pages.

Zakhari, S. "Overview: How is Alcohol Metabolized by the Body?" NIH-NIAAA archived online May 27, 2010, 12 pages.

U.S. Appl. No. 14/236,531 Notice of Allowance mailed Mar. 16, 2015, 7 pages.

U.S. Appl. No. 14/236,531 Notice of Allowance mailed Jun. 26, 2015, 7 pages.

U.S. Appl. No. 14/236,531 Office Action mailed Aug. 1, 2014, 16 pages.

U.S. Appl. No. 14/236,531 Response to Office Action filed Jan. 31, 2015, 14 pages.

Adachi, K., et al; Purification and properties of homogentisate oxygenase from Pseudomonas fluorescens. Biochim. Biophys. Acta 118 (1966) 88-97.

Aldridge, W.N.; Serum esterases. I. Two types of esterase (A and B) hydrolysing p-nitrophenyl acetate, propionate and butyrate and a method for their determination. Biochem. J. 53 (1953) 110-117.

Amitai, G. et al.; Enhanced stereoselective hydrolysis of toxic organophosphates by directly evolved variants of mammalian serum paraoxonase; FEBS Journal 273 (2006) pp. 1906-1919.

Augusteyn, R.C., et al; On the homology of the active-site peptides of liver Carboxylesterases. Biochim. Biophys. Acta 171 (1969) 128-137.

Augustinsson, K.-B. and Heimburger, G. Enzymatic hydrolysis of organophosphorus compounds. I. Occurrence of enzymes hydrolysing dimethyl-amido-ethoxy-phosphoryl cyanide (Tabun). Acta Chem. Scand. 8 (1954) 753-761.

Bertoni, G., et al; "Cloning of the Genes for and Characterization of the Early Stages of Toluene and o-Xylene Catabolism in Pseudomonas stutzeri OX1," Applied and Environmental Microbiology, 1996, 62(10): pp. 3704-3711.

(56) References Cited

OTHER PUBLICATIONS

Bertoni, G., et al; "Analysis of the Gene Cluster Encoding Toluene/o-Xylene Monooxygenase from Pseudomonas stutzeri OX1," Applied and Environmental Microbiology, 1998. 64(10): pp. 3626-3632.

Buchinger, P.J. et al.; Characteristics of Microbial Assay for the Detection of Halogenated Hydrocarbons Using Cells of an Actinomycete-like Organism as a Biological Component; Acta Biotechnol. 17 (1997) 2, 123-130.

Byrne, A.M., et al; "Sequence Analysis of the Gene Cluster Encoding Toluene-3-monooxygenase from Pseudomonas pickettii PK01," Gene, 1995. 154: pp. 65-70.

Cardini, G. & Jurtshuk, P. The enzymatic hydroxylation of n-octane by *Corynebacterium* sp. strain 7E1C. J. Biol. Chem. 245 (1970) 2789-2796.

Cardy, D.L.N., V. Laidler, G.P.C. Salmond, and J.C. Murrell, "Molecular Analysis of the Methane Monooxygenase (MMO) Gene Cluster of Methylosinus trichosporium OB3b," Molecular Microbiology, 1991. 5(2): pp. 335-342.

Chang, K. H., et al; Isolation and characterization of the three polypeptide components of 4-chlorobenzoate dehalogenase from *Pseudomonas* sp. strain CBS-3. Biochemistry 31 (1992) 5605-5610.

Chopra, I. J. & Teco, G. N. C. Characteristics of inner ring (3 or 5) monodeiodination of 3,5-diiodothyronine in rat liver: evidence suggesting marked similarities of inner and outer ring deiodinases for iodothyronines. Endocrinology 110 (1982) 89-97.

Colby, J. et al; The soluble methane mono-oxygenase of Methylococcus capsulatus (Bath). Its ability to oxygenate n-alkanes, n-alkenes, ethers, and alicyclic, aromatic and heterocyclic compounds. Biochem. J. 165 (1977) 395-402.

Crooks, G. P. & Copley, S. D.; Purification and characterization of 4-chlorobenzoyl CoA dehalogenase from *Arthrobacter* sp. strain 4-CB1. Biochemistry, 33 (1994) 11645-11649.

de Souza, M. L. et al; Cloning, characterization, and expression of a gene region from *Pseudomonas* sp. strain ADP involved in the dechlorination of atrazine. Appl. Environ. Microbiol. 61 (1995) 3373-3378.

de Souza, M. L., et al; Atrazine chlorohydrolase from *Pseudomonas* sp. strain ADP: gene sequence, enzyme purification, and protein characterization. J. Bacteriol. 178 (1996) 4894-4900.

Dodgson, K.S., et al; Studies on sulphatases. 13. The hydrolysis of substituted phenyl sulphates by the arylsulphatase of Alcaligenes metacaligenes. Biochem. J. 64 (1956) 216-221.

Ensley, B.D. & Gibson, D.T. Naphthalene dioxygenase: purification and properties of a terminal oxygenase component. J. Bacteriol. 155 (1983) 505-511.

Fetzner, S., et al; Degradation of 2-chlorobenzoate by Pseudomonas cepacia 2CBS. Biol. Chem. Hoppe-Seyler 370 (1989) 1173-1182.

Fox, B.G., et al., "Methane Monooxygenase from Methylosinus trichosporium OB3b," Journal of Biological Chemistry, 1989. 264(17): pp. 10023-10033.

Fujisawa, H. & Hayaishi, O.; Protocatechuate 3,4-dioxygenase. I. Crystallization and characterization. J. Biol. Chem. 243 (1968) 2673-2681.

Goldman, P. & Milne, G. W. A.; Carbon-fluorine bond cleavage. II. Studies on the mechanism of the defluorination of fluoroacetate. J. Biol. Chem. 241 (1966) 5557-5559.

Goldman, P., et al.; Carbon-halogen bond cleavage. 3. Studies on bacterial halidohydrolases. J. Biol. Chem. 243 (1968) 428-434.

Goldman, P.; The enzymatic cleavage of the carbon-fluorine bond in fluoroacetate. J. Biol. Chem. 240 (1965) 3434-3438.

Goswam A., et al.; Inhibition by coumadin anticoagulants of enzymatic outer ring monodeiodination of iodothyronines. Biochem. Biophys. Res. Commun. 104 (1982) 1231-1238.

Hayaishi, O. & Sutton, W.B. Enzymatic oxygen fixation into acetate concomitant with the enzymatic decarboxylation of L-lactate. J. Am. Chem. Soc. 79 (1957) 4809-4810.

Heppel, L. A. & Porterfield, V. T. Enzymatic dehalogenation of certain brominated and chlorinated compounds. *J. Biol. Chem.* 176 (1948) 763-769.

Hosokawa, K. & Stanier, R.Y. Crystallization and properties of p-hydroxybenzoate hydroxylase from Pseudomonas putida. J. Biol. Chem. 241 (1966) 2453-2460.

Junker, F., et al; Dioxygenation and spontaneous deamination of 2-aminobenzene sulphonic acid in *Alcaligenes* sp. strain O-1 with subsequent meta ring cleavage and spontaneous desulphonation to 2-hydroxymuconic acid. Biochem. J. 300 (1994) 429-436.

Keuning, S., Janssen, D. B. & Witholt, B.; Purification and characterization of hydrolytic haloalkane dehalogenase from Xanthobacter autotrophicus GJ10; J. Bacteriol. 163 (1985) 635-639.

Kohler-Staub, D. & Leisinger, T.; Dichloromethane dehalogenase of *Hyphomicrobium* sp. strain DM2. J. Bacteriol. 162 (1985) 676-681.

Kumagai, H., et al; S-Carboxymethylcysteine synthase from *Escherichia coli*. Agric. Biol. Chem. 53 (1989) 2481-2487.

Lipke, H. & Kearns, C. W.; DDT dechlorinase. I. Isolation, chemical properties, and spectrophotometric assay. J. Biol. Chem. 234 (1959) 2123-2128.

Lipke, H. & Kearns, C. W.; DDT dechlorinase. II. Substrate and cofactor specificity. J. Biol. Chem. 234 (1959) 2129-2132.

McClay, K., B.G. Fox, and R.J. Steffan, "Chloroform Mineralization by Toluene-Oxidizing Bacteria," Applied and Environmental Microbiology, 1996. 62(8): pp. 2716-2722.

Moorefield, H. H. Purification of DDT-dehydrochlorinase from resistant houseflies. Contr. Boyce Thompson Inst. 18 (1956) 303-310.

Moriguchi, M., et al.; Dehalogenation and deamination of 1-2-amino-4-chloro-4-pentenoic acid by Proteus mirabilis. Agric. Biol. Chem. 51 (1987) 3295.

Motosugi, M., et al.; Preparation and properties of 2-halo acid dehalogenase from Pseudomonas putida. Agric. Biol. Chem. 46 (1982) 837-838.

Mulchandani, A. et al.; Biosensor for Direct Determination of Organophosphate Nerve Agents Using Recombatant *Escherichia coli* with Surface-Expressed Organophosphorus Hydrolase.—2. Fiber-Optic Microbial Bionsenor; ., Analytical Chemistry 1998 70 (23), 5042-5046.

Muller, C. et al.; Multicomponent fiberoptical biosensor for use in hemodialysis monitoring; SPIE Biomedical Fiber Optic Instrumentation; vol. 2131; pp. 555-562 (Jul. 1994).

Muller, R., et al.; Incorporation of [18O] water into 4-hydroxybenzoic acid in the reaction of 4-chlorobenzoate dehalogenase from *Pseudomonas* sp. CBS 3. Biochem. Biophys. Res. Commun. 124 (1984) 178-182.

Nagasawa, T.,et al.; Physiological comparison of D-cysteine desulfhydrase of *Escherichia coli* with 3-chloro-D-alanine dehydrochlorinase of Pseudomonas putida CR 1-1. Arch. Microbiol. 149 (1988) 413-416.

Nakagawa, H. and Takeda, Y. Phenol hydroxylase. Biochim. Biophys. Acta 62 (1962) 423-426.

Nordlund, I., et al., "Complete nucleotide sequence and polypeptide analysis of multicomponent phenol hydroxylase from Pseudomonas strain CF600," Journal of Bacteriology, 1990. 172: pp. 6826-6833.

PCT/US2002/017407 International Search Report; mailed Sep. 24, 2003; 2 pages.

PCT/US2009/040121, International Search Report & Written Opinion mailed Jul. 14, 2009, 7 Pages.

Pikus, J.D., et al; "Recombinant Toluene-4-Monooxygenase: Catalytic and Mossbauer Studies of the Purified Diiron and Rieski Components of a Four-Protein Complex," Biochemistry, 1996. 35: pp. 9106-9119.

Ramanathan, M. & Simonian, A.L.; Array biosensor based on enzyme kinetics monitoring by fluorescence spectroscopy: Application for neurotoxins detection; Biosensors and Bioelectronics 23 (2007) pp. 3001-3007.

Renganathan, V. Possible involvement of toluene-2,3-dioxygenase in defluorination of 3-fluoro-substituted benzenes by toluene-degrading *Pseudomonas* sp. strain T-12. Appl. Exp. Microbiol. 55 (1989) 330-334.

Rosenzwieg, A.C., et al. "Geometry of the Soluble Methane Monooxygenase Catalytic Diiron Center in Two Oxidation States," Chemistry and Biology, 1995. 2(6): pp. 409-418.

(56) References Cited

OTHER PUBLICATIONS

Schenk, T., et al.; Enzymatic dehalogenation of pentachlorophenol by extracts from *Arthrobacter* sp. strain ATCC 33790. J. Bacteriol. 171 (1989) 5487-5491.
Scholtz, R., et al.; Characterization of 1-chlorohexane halidohydrolase, a dehalogenase of wide substrate range from an *Arthrobacter* sp. J. Bacteriol. 169 (1987) 5016-5021.
Simonian, AL., et al.; FET-Based Biosensors for the Direct Detection of Organophosphate Neurotoxins; Electroanalysis 2004; 16, No. 22; pp. 1896-1906.
Smallridge, R. C., et al. "3',5'-Diiodothyronine to 3'-monoiodothyronine conversion in the fed and fasted rat: enzyme characteristics and evidence for two distinct 5'-deiodinases" Endocrinology 108 (1981) 2336-2345.
Stainthorpe, A.C., et al., "The Methane Monooxygenase Gene Cluster of Methylococcus capsulatus (Bath)," Gene, 1990. 91: pp. 27-34.
Suzuki, K., Takemori, S. and Katagiri, M. Mechanism of the salicylate hydroxylase reaction. IV. Fluorimetric analysis of the complex formation. Biochim. Biophys. Acta 191 (1969) 77-85.
Yamada, H., et al; Synthesis of D-cysteine from 3-chloro-D-alanine and hydrogen sulfide by 3-chloro-D-alanine hydrogen chloride-lyase (deaminating) of Pseudomonas putida. Biochem. Biophys. Res. Commun. 100 (1981) 1104-1110.
Yen, K.-M., "Construction of Cloning Cartridges for Development of Expression Vectors in Gram-Negative Bacteria," J. Bacteriol., 1991. 173(17): pp. 5328-5335.
Yokota, T., et al.; Purification and properties of haloalkane dehalogenase from *Corynebacterium* sp. strain m15-3. J. Bacteriol. 169 (1987) 4049-4054.
Ziegler, D.M. and Pettit, F.H. Microsomal oxidases. I. The isolation and dialkylarylamine oxygenase activity of pork liver microsomes. Biochemistry 5 (1966) 2932-2938.
Conzuelo, F. et al., An Integrated amperometric biosensor for the determination of lactose in milk and dairy products, J. Agric. Food Chern., Jun. 23, 2010, pp. 7141-7148.
Jenkins, D.M. et al. Adaptation of a manometric biosensor to measure glucose and lactose, Biosensors Bioelectronics, Jan. 31, 2003, pp. 101-107.
Plata, M.R. et al., State-of-the-art of (bio)chemical sensor developments in analytical spanish groups , Sensors, Mar. 24, 2010, pp. 2511-2576.
PCT/US11/61956 International Search Report and Written Opinion mailed Jun. 14, 2012, 10 pages.
PCT/US12/49384 International Search Report and Written Opinion mailed Feb. 20, 2012, 11 pages.
PCT/US12/58331 International Search Report and Written Opinion mailed Mar. 29, 2013, 11 pages.
PCT/US02/17407, International Preliminary Examination Report, Mar. 5, 2005, 4 pages.
Zhong, Z. et al., Fiber optic monooxygenase biosensor for toluene concentration measurement in aqueous samples, Biosensors and Bioelectronics 26 (2011) 2407-2412.
U.S. Appl. No. 10/478,822.
U.S. Appl. No. 12/100,308.
U.S. Appl. No. 12/358,140.
Mills, A. et al., Reversible, fluorescence-based optical sensor for hydrogen peroxide. Analyst 132 2007) 566-571.
Posch, H.E. & Wolfbeis. O.S., Optical sensor for hydrogen peroxide. Microchimica Acta 97 (1989) 41-50.
Rajendran, V., Lrudayaraj, J. Detection of glucose, galactose, and lactose in milk with a microdialysis-coupled flow injection amperometric sensor. J Dairy Sci. 85 (2002) 1357-61.
Pilloton, R et al., Lactose Determination in Raw Milk with a Two-Enzyme Based Electrochemical Sensor. Analytical Letters. 20 (1987) 1803-1814.
Tkác J, et al., Novel glucose non-interference biosensor for lactose detection based on galactose oxidase-peroxidase with and without co-immobilised beta-galactosidase. Analyst. 125 (2000) 1285-9.
Wichmann, R. & Vasic-Racki. D., Cofactor Regeneration at the Lab Scale. Adv Biochem Engin/Biotechnol 92 (2005) 225-260.
Zhao, H & van der Donk, W.A.. Regeneration of cofactors for use in biocatalysis. Current Opinion in Biotechnology. 14 (2003) 583-589.
Woodyer, R.D. et al. (2005) Regeneration of cofactors for enzyme biocatalysis. Enzyme Technology, 85-103.
Johannes, T.W. et al. (2005). Directed evolution of a thermostable phosphite dehydrogenase for NAD(P)H regeneration. Applied and Environmental Microbiology, 71(10), 5728-5734. doi:10.1128/AEM.71.10.5728-5734.2005.
Snaked, Z. & Whitesides, G.M., Enzyme-catalyzed organic synthesis: NADH regeneration by using formate dehydrogenase. J. Am. Chem. Soc. 102 (1980) 7104-7105.
Berríos-Rivera, .S.J. et al. Metabolic engineering of *Escherichia coli*: increase of NADH availability by overexpressing an NAD(+)-dependent formate dehydrogenase. Metab Eng. 4 (2002) 217-29.
Al-Raweshidy, H.S., et al. Electro-optic correlation in a spread specrum multiplexing system for fibre optic interferometers, Optics Communications 81 Feb. 15, 1991, pp. 171-174.
U.S. Appl. No. 13/562,592 Non-Final Rejection dated Oct. 8, 2015, 20 pages.
Chudobova, Ivana et al, "Fibre optic biosensor for the determination of D-glucose based on absorption changes of immobilized glucose oxidase," Analytica Chimica Acta, Issue 319 (1996) pp. 103-110.
Ferri, et al., "Review of Glucose Oxidases and Glucose Dehydrogenases: A Bird's Eye View of Glucose Sensing Enzymes," Journal of Diabetes Science and Technology, vol. 5, Issue 5 (Sep. 2011), pp. 1068-1076.
Godfrey, Larry "Choosing the Detector for your Unique Light Sensing Application" EG&G Optoelectronics Data Sheet, 1997, 6 pages.
Issue Notification; May 14, 2008, for U.S. Appl. No. 10/478,822, 1 page.
Lipson, D. et al., Multifiber, Multiwavelength, Fiber Optic Flourescence Spectrophotometer, IEEE Trans. Biomed. Eng. vol. 39, No. 9 Sep. 1992, pp. 886-892.
Mills, "Optical Oxygen Sensors, Utilising the Luminescence of Platinum Metals Complexes," Platinum Metals Review, vol. 41, Issue 3 (1997) pp. 115-127.
Moreno-Bondi, Maria C., et al., Oxygen Optrode for Use in a Fiber-Optic Glucose Biosensor, Analytical Chemistry, vol. 62, No. 21 (Nov. 1, 1990), pp. 2377-2380.
Notice of Allowance mailed Jan. 13, 2012, for U.S. Appl. No. 12/358,140, 7 pages.
Notice of Allowance mailed Feb. 13, 2008, for U.S. Appl. No. 10/478,822, 3 pages.
Office Action mailed Apr. 1, 2011, for U.S. Appl. No. 12/358,140, 8 pages.
Office Action mailed Oct. 28, 2011, for U.S. Appl. No. 12/358,140, 9 pages.
Office Action mailed Oct. 31, 2007, for U.S. Appl. No. 10/478,822, 6 pages.
Office Action mailed May 17, 2007, for U.S. Appl. No. 10/478,822, 13 pages.
Response to Office Action filed Aug. 1, 2011, for U.S. Appl. No. 12/358,140, 15 pages.
Response to Office Action filed Dec. 28, 2007, for U.S. Appl. No. 10/478,822, 10 pages.
Response to Office Action filed Dec. 28, 2011, for U.S. Appl. No. 12/358,140, 27 pages.
Response to Office Action filed Aug. 17, 2007, for U.S. Appl. No. 10/478,822, 79 pages.
Response to Restriction Requirement filed Feb. 12, 2007, for U.S. Appl. No. 10/478,822, 6 pages.
Restriction Requirement mailed Jan. 12, 2007, for U.S. Appl. No. 10/478,822, 4 pages.
Schaffar, Bernhard P.H., et al., "A Fast Responding Fibre Optic Glucose Biosensor Based on an Oxygen Optrode," Biosensors & Bioelectronics, Issue 5 (1990), pp. 137-148.
Steiner, Mark-Steven, et al., "Optical methods for sensing glucose," Chemical Society Reviews, Issue 9 (Sep. 1, 2011), pp. 4805-4839.

(56) References Cited

OTHER PUBLICATIONS

Sundari, et al., "Retention of enzyme activity following freeze-drying the mycelium of ectomycorrhizal isolates: part II. Enzymes acting upon carbon compounds," World Journal of Microbiology and Biotechnology, vol. 16 (2000), pp. 865-868.

Trettnak, Wolfgang, et al., "A Fiberoptic Cholesterol Biosensor with an Oxygen Optrode as the Transducer," Analytical Biochemistry, Issue 184 (1990) pp. 124-127.

Trettnak, Wolfgang, et al., "Fibre Optic Glucose Biosensor With an Oxygen Optrode as the Transducer," Analyst, vol. 113 (Oct. 1988) pp. 1519-1523.

Trettnak, Wolfgang, et al., "Fibre-Optic Glucose Sensor with a pH Optrode as the Transducer," Biosensors, Issue 4 (1988), pp. 15-26.

van Beilen, et al., "Practical issues in the application of oxygenases," TRENDS in Biotechnology, vol. 21, No. 4, Apr. 2003, pp. 170-177.

Vilker, et al., "Challenges in Capturing Oxygenase Activity in Vitro," Journal of the American Oil Chemists' Society, vol. 76, No. 11 (1999), pp. 1283-1289.

Wilson, et al., "Glucose oxidase: an ideal enzyme," Biosensors & Bioelectronics, vol. 7 (1992), pp. 165-185.

\* cited by examiner

ENZYMATIC BIOSENSING SYSTEMS

RELATED APPLICATIONS

This application is a continuation-in-part of U.S. patent application Ser. No. 12/100,308, filed Apr. 9, 2008, which claimed the benefit of priority to U.S. Provisional Patent Application Ser. Nos. 60/922,496, filed Apr. 9, 2007, and 61/024,453, filed Jan. 29, 2008, and which was a continuation-in-part of U.S. patent application Ser. No. 10/478,822 filed Aug. 9, 2004, now U.S. Pat. No. 7,381,538, which was a national phase entry under 35 U.S.C. §371 of PCT/US02/17407, filed Jun. 1, 2002, which claimed the benefit of priority to U.S. Provisional Patent Application Ser. No. 60/295,211, filed Jun. 1, 2001.

GOVERNMENT RIGHTS

This invention was made with Government support under contract number BES-0529048 awarded by the National Science Foundation and contract number DACA71-01-C-0009 awarded by the U.S. Army Research Office. The U.S. Government has certain rights in this invention.

BACKGROUND

In general, the present invention relates to techniques for monitoring halogenated organic chemicals (pollutants, pesticides, etc.) in soil, as well as groundwater, waste waters, and other aqueous environments. More particularly, the invention is directed to an improved distal tip having a transducer to which a biocomponent comprising a dehalogenase (selected for dehalogenation of a selected analyte of interest) is immobilized, treated, and/or stabilized for monitoring continuously in situ soil or an aqueous environment to detect the presence and/or concentration of the analyte, such as any of the s-triazine pesticides, including the chlorinated herbicide atrazine (used to control broadleaf and grassy weeds), simazine, terbuthylazine, propazine, cyanazine, deethylatrazine, and deisopropylatrazine, plus other s-triazines (including those in TABLE 1), lindane, and DDT. Disclosed is a novel technique of measuring an analyte and associated biosensor capable of measuring pH (hydrogen ion) and halide ion concentration in soil and aqueous environments to detect the concentration, or collect other information about, the analyte. In one aspect of the invention, focus is on a unique biosensor including a fiber optic element (an optical fiber or bundle), the tip of which has a layer of a bacteria atop a layer of a pH-sensitive fluorophore (dye). The bacteria is selected such that it carries an enzyme to catalyze a reaction with the halogenated compound of the analyte, releasing either protons (and causing a detectable pH change) or a measurable halide ion concentration. Further, prior to being 'glued' (immobilized or otherwise affixed) to the tip of the fiber optic transducer, the bacteria layer is specially treated and/or stabilized.

Currently available techniques to measure analytes, and more-particularly pollutants, in groundwater include ex situ laboratory measurements which generally have a long response time and are expensive, or use of immunoassay kits which can be quite inaccurate and also expensive. In Campbell, 1998 entitled "The Development of Biosensors for the Detection of Halogenated Groundwater Contaminants" Spring 1998, submitted by D. W. Campbell in fulfillment of the requirements for the Degree of Master of Science at Colorado State University, available from Morgan Library at the Colorado State University in Fort Collins, Colo., reference is made to a pH optode structure featuring the reaction illustrated schematically in Campbell, 1998 (labeled FIG. 2.4): the cleavage of halide ion X– and proton H+ from a halogenated hydrocarbon by the appropriate hydrolytic dehalogenase. An earlier reference entitled "Multicomponent fiberoptical biosensor for use in hemodialysis monitoring" (Cord Müller, et al.) employed a pH optode-type biosensor structure limited to the use of urease as a catalyst (urea is split into ammonia & $CO_2$): the bifunctional reagent glutaraldehyde was used to bind the urease directly to the head of a pH optode.

Chemical biosensors are miniaturized analytical devices, which can deliver real-time and on-line information on the presence of specific compounds or ions in complex samples. Usually an analyte recognition process takes place followed by the conversion of chemical information into an electrical or optical signal. Two popular classes of chemical sensors used today are electrochemical transduction type (amperometric, potentiometric, including ion-selective electrodes (ISE), field effect transistors (FETs), gas-sensing electrodes, etc., and conductimetric) and optical transduction type (including pH optodes). They are used during laboratory analysis as well as in industry, process control, physiological measurements, and environmental monitoring. The basic principles of operation of the chemical sensors utilizing electrochemical and optical transduction are quite well understood. In developing biosensors for general manufacture and commercial use, longevity and stabilization of the biocomponent are critical. It is preferable to have a stable, long-lived biosensor that can stand prolonged storage as well as perform well in use for a selected period of time. Among the biocomponent possibilities, enzymes, though very selective, fall on the lower end of the 'stability spectrum'.

The s-triazine compounds include many pesticides. Within the s-triazine family (which includes both pesticides and non-pesticide groups, see TABLE 1), atrazine is most widely used, although others include simazine, terbuthylazine, propazine, cyanazine, deethylatrazine, and deisopropylatrazine as well as others in FIG. 1, a depiction of several pathways derived from general knowledge of atrazine degradation. S-triazines are characterized by a symmetrical hexameric ring consisting of alternating carbon and nitrogen atoms.

TABLE 1

Non-pesticide s-triazine groups with comments about use and biodegradability.

| | |
|---|---|
| 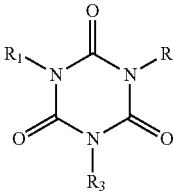 Cyanuric acid | Cyanuric (isocyanuric) acids: N-Chlorination of Cyanuric acid at the R1, R2, and R3 sites yields chloroisocyanurates that are used as disinfectants (in swimming pools and hot-tubs), sanitizers (in household cleansers and automatic dishwashing compounds), and bleaches (in both the industrial and household bleaching of fabrics). The most common chloroisocyanurates are Trichloro and Dichloro isocyanuric acid (TCCA, DCCA) and Sodium dichloroisocyanuric acid (SDCC). |
| 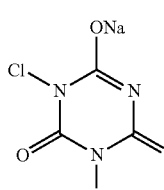 SDCC | Triallyl isocyanurate (R1, R2, and R3 = propenyl) is used as a crosslinking agent for poly (vinyl chloride) and other systems. Methylamine (also on the metapathway map) and N-substituted methylamines are sometimes used as finishing agents for textiles. |

TABLE 1-continued

Non-pesticide s-triazine groups with comments about use and biodegradability.

| | |
|---|---|
| 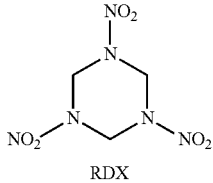  RDX | Nitramine explosives: Cyclotrimethylene-trinitramine (RDX) is an explosive and a propellant used in military rockets. The partial biodegradation of RDX by mixed microbial culture is reported in (Binks et al 1995). |
| 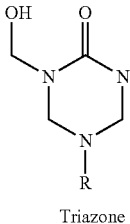  Triazone | Triazone: A cyclic urea used as a cross linking agent in textile finishing. 1,3-dimethylol-5-alkyltriazone is still widely used for this purpose. Cross linking agents are used in the preparation of textiles to induce "memory" and to add luster. |

SUMMARY

It is a primary object of the invention to provide structure and a method of producing a distal tip of a biosensor ion sensing transducer for use in detecting an analyte comprising a halogenated organic compound in an environment such as soil or an aqueous environment. The biocomponent being immobilized, treated, and stabilized accordingly.

As can be appreciated, the innovative biosensor, a distal tip of which has an ion sensing transducer for use in detecting an analyte and a biocomponent comprising a dehalogenase such as an enzyme selected from the hydrolases, class EC 3.8, or lyases, class EC 4.5, for carrying out a dehalogenation of the analyte—as contemplated and described herein—can accommodate a variety of enzymatic activities and distal tip structures, including features claimed herein, all within the spirit and scope of this disclosure. Advantages include, without limitation:

(a) Disposable use with real-time results—The invention may be used for single- or multiple-use applications, or for continuous real-time monitoring over a selected time period, of an aqueous or soil environment.

(b) Simplicity and versatility—The invention may be used to collect information about physical properties of a wide range of analytes without requiring sophisticated equipment and complicated procedures. Simplicity of design can lead to reduced fabrication costs making kits economically feasible for handy off-site use—allowing information to be readily available.

(c) Structural design—The unique combination of immobilization and stabilizing features provide a robust distal tip design.

(d) Several biosensor tips having similar transducer types (optical or electrochemical) may be incorporated into a bundle providing a package of different types of information relating to the environment by sampling simultaneously or sequentially.

Briefly described, once again, the invention includes a distal tip of a biosensor ion sensing transducer for use in detecting an analyte comprising an halogenated organic compound in an environment such as soil or an aqueous environment. The ion-sensing transducer is preferably selected from the following: a pH optode, a pH electrode, a field-effect transistor (FET), and an halide ion-selective electrode (ISE). Analytes of interest are many, including, without limitation: s-triazine compounds including those developed for use as pesticides such as atrazine, simazine, terbuthylazine, propazine, cyanazine, deethylatrazine, and deisopropylatrazine, and others including those listed in TABLE 1; beta-, or the more common, gamma-hexachlorocyclohexane ("Lindane"); and DDT (1,1,1-trichloro-2,2-bis(p-chlorophenyl)ethane). Microorganisms that can initiate pathways as identified in TABLE 3 are for the widely used herbicide atrazine (degradation example shown in FIG. 2), without limitation these include: *Pseudomonas* sp. ADP; *Ralstonia* sp. M91-3; *Clavibacter michiganese* sp. ATZ1; *Agrobacterium* sp. J14a; *Alcaligenes* sp. SG1; and *Rhodococcus* spp. NI86/21, TE1; *Pseudomonas* spp. 192, 194; and *Streptomyces* sp. PS1/5.

Key features of the distal tip include: a biocomponent comprising at least one enzyme for carrying out a dehalogenation of the compound; the biocomponent is immobilized to a surface of the tip; a treatment of the biocomponent for maintaining a period of enzymatic efficacy; and the biocomponent stabilized by means preferably selected from the group consisting of crosslinking a surface of the immobilized biocomponent, crosslinking a polymer layer to the biocomponent, adding a gel-hardening agent to the biocomponent, adding a stabilizing agent to the biocomponent, and modifying a component of the immobilizing means. Immobilization is preferably carried out by means selected from the group consisting of (a) entrapment within a hydrogel; (b) entrapment within a polymeric network; (c) (micro)encapsulation; (d) covalent-bonding; and (e) adsorption. The dehalogenase may be selected from the group consisting of hydrolases, subclass EC 3.8, and lyases, subclass EC 4.5 as listed in TABLE 2A. One might choose to target a dehalogenase which (1) produces a measurable pH change and (2) needs no reactant other than the halogenated analyte (e.g., atrazine) and perhaps water—thus excluding the reductive dehalogenases, which require something to oxidize while they reduce the halogenated analyte, and other classes of enzymes that require oxygen or energy from the cell.

Associated with the biosensor structural features, the invention also covers a method of producing a biosensor distal tip having an ion sensing transducer and a biocomponent for use in detecting an analyte (an halogenated organic compound) in an environment. In a first characterization of the method of the invention, steps include: immobilizing the biocomponent having at least one enzyme for carrying out a dehalogenation of the compound, to a surface of the tip by means selected from the group consisting of (a) entrapping the enzyme within a hydrogel secured to the tip surface; (b) entrapping the enzyme within a polymeric network secured to the tip surface; (c) (micro)encapsulating the enzyme; (d) covalent-bonding a second component of the biocomponent to the tip surface; (e) cross-linking the enzyme to a support material secured to the tip surface; and (f) adsorbing the enzyme into the tip surface; treating the biocomponent for maintaining a period of enzymatic efficacy; and stabilizing the biocomponent by means selected from the group consisting of crosslinking a polymer layer to the biocomponent, adding a gel-hardening agent to the biocomponent, adding a stabilizing agent to the biocomponent, and modifying a component of the immobilizing means.

Further distinguishing features of the biosensor distal tip and method of the invention are many. The hydrogel or polymeric matrix used for entrapment of the dehalogenase— in the form of pure enzymes or within cells (whether naturally occurring or recombinant) may be selected as follows: suitable hydrogels include algal polysaccharides (such as agar, agarose, alginate, and K-carrageenan), gelatin, collagen, pectin, poly(carbamoyl) sulfonate, locust bean gum, and gellan; and suitable polymers include polyacrylamide, polystyrene, polymethacrylate, polyvinylalcohol and polyurethane. The biocomponent treatment may be selected from the following: applying an inhibitor of protein synthesis, adding a protease inhibitor, freeze drying, and dry heating. Further focusing on particular features: (1) the protein synthesis inhibitor may include any suitable antibiotic such as one selected from the following types: chloramphenicol, aminoglycosides (e.g., kanamycin), tetracyclines, and macrolides (e.g., erythromycin); (2) the polymer layer crosslinked for stabilization may be selected from suitable polymers including poly-L-lysine (PLL), polyethylenimine, polyacrylic acid, polyvinyl alcohol, polyacrylamide, and polyurethane; (3) a crosslinking agent such as glutaraldehyde may be used for the crosslinking of the biocomponent surface; (4) a suitable polyalcohol or sugar may be selected for adding to the biocomponent as a stabilizing agent.

In one aspect, presently disclosed is a biosensor for measuring the concentration of a molecule in a solution with a fiber optical cable having a first end and a second end, and a transducer layer having a first side and a second side, and a matrix layer having a first side and a second side, and a biocomponent disposed within said matrix layer; wherein the first end of said fiber optical cable is bound to said second side of said transducer layer; and wherein the first side of the transducer layer is bound to the second side of the matrix layer; and wherein the first side of the matrix layer is in contact with the solution; and wherein the second end of the fiber optical cable is coupled to an optical excitation source, a photon detection device, an electronic amplification device, signal processing circuitry and a signal output device. In one embodiment, the biosensor has a transducer layer that is an optical transducer selected from an ultraviolet-visible absorption transducer, a luminescence transducer, a fluorescence transducer, a phosphorescence transducer, an emission transducer, a bioluminescence transducer, a chemiluminescence transducer, an internal reflection spectroscopy transducer, and a laser light scattering methods transducer. In one embodiment, the biosensor contains a luminescence transducer selected from trisodium 8-hydroxy-1,3,6-trisulphonate, fluoro (8-anilino-1-naphthalene sulphonate), tris (bipyridine)ruthenium(II) complex, ruthenium complexes, and acridinium- and quinidinium-based reagents. In one embodiment, the biosensor has a matrix layer that is a hydrogel and the hydrogel is selected from algal polysaccharides, agarose, alginate, gelatin, collagen, pectin, poly (carbamoyl) sulfonate, locust bean gum, and gellan. In an embodiment, the biosensor matrix layer is a polymer. In an embodiment, the biosensor matrix layer is a polymer selected from polyacrylamide, polystyrene, polymethacrylate, polyvinylalcohol and polyurethane. In one embodiment, the biosensor is stabilized from chemical degradation by using various techniques including adding inhibitors of protein synthesis, adding protease inhibitors, freeze drying the biocomponent, and dry heating the biocomponent. In one embodiment, the first end of the fiber optical cable is coated with a layer of molecules selected from cellulose acetate, polycarbonate, collagen, acrylate copolymers, poly(ethylene glycol), polytetrafluoroethylene, and alginate-polylysine-alginate microcapsules. In one embodiment, the biocomponent of the biosensor is adsorbed within the matrix by physisorption or chemisorption. In one embodiment, the biocomponent is bound to the matrix through adding crosslinking agents to the biocomponent that is disposed within the matrix; and wherein the crosslinking agents are selected from glutaraldehyde, hexamethylene diisocyanate and 1,5-dinitro-2,4-difluorobenzene. In one embodiment, the biosensor transducer layer is covalently bound to a layer of molecules which are bound to the first end of the fiber optical cable, the molecules are selected from cellulose, cellulose derivatives, silica, glass, dextran, starch, agarose, porous silica, chitin and chitosan. In one embodiment, the biosensor has a bioluminescence transducer that is luciferin. In one embodiment, the biosensor has a internal reflection spectroscopy transducer that generates an evanescent wave. In one embodiment, the biosensor has a laser-light-scattering-methods-transducer that is selected from quasi-elastic light-scattering spectroscopy, photon correlation spectroscopy and laser Doppler velocimetry. In one embodiment, the biocomponent is stabilized against chemical degradation by grafting a molecule onto the biocomponent. The molecule is selected from polysaccharides, polyalcohols, trehalose, maltose, lactose, sucrose, glucose and galactose. In one embodiment, the biocomponent is immobilized within the matrix by crosslinking the biocomponent to the matrix with crosslinking agents selected from glutaraldehyde, polyethyleneimine, hexamethylenediamine and formaldehyde. In one embodiment, the biosensor has a capillary tube having a first end and second end; wherein the second end of the capillary tube is coupled to a source of a molecule and the first end of the capillary tube is coupled to the matrix layer; and wherein the molecule is delivered into the matrix layer through the capillary tube. In one embodiment, the capillary tube contains oxygen. In one embodiment, the capillary tube contains hydrogen peroxide. In one embodiment, the capillary tube contains a substrate for the biocomponent. In one embodiment, the biosensor has an optical excitation source that is selected a halogen lamp, a laser, and a light emitting diode. In one embodiment, the biosensor has an electronic amplification device with a photomultiplier tube, an avalanche photodiode, and a p-i-n photodiode having an integrated amplifier. In one embodiment, the biosensor of has a biocomponent that is an enzyme. In one embodiment, the biocomponent of the biosensor is encoded for by a nucleotide coding sequence of the biocomponent enzyme that is part of a plasmid that is within a whole cell and wherein the whole cell is a within the matrix of the biosensor. In one embodiment, the biocomponent of the biosensor is encoded by a nucleotide coding sequence of the biocomponent enzymes that is part of the chromosome of a whole cell and the whole cell is within the matrix of the biosensor. In one embodiment, the biosensor has a biocomponent that is a purified enzyme. In one embodiment, the biosensor has whole cell biocomponents that are alive. In one embodiment, the biosensor has whole cell biocomponents that are dead. In one embodiment, the biosensor transducer layer is an optical transducer that interacts with oxygen. In one embodiment, the biosensor transducer layer is an optical transducer that interacts with protons. In one embodiment, the biosensor transducer layer is an optical transducer that interacts with halide ions. In another embodiment, the biosensor is arranged as an array of biosensors wherein each biosensor contains a different biocomponent or mixture of biocomponents; and wherein each of the biocomponents interacts with one type of transducer. In one embodiment, the biosensor biocomponent has a different substrate specificity for each member of a group of compounds; wherein the difference in substrate specificity of each of the biocomponents in an array is used to determine individual concentrations of each member of the group of compounds. In one embodiment, the biosensors in an array are individually coupled to an optical excitation source, a photon detection device, an electronic amplification device, and signal processing circuitry through an optical fiber; wherein the signal processing circuitry detects the signal from each of the biosensors in the array. In one embodiment, the biosensors in an array are coupled to an optical excitation source, a photon detection device, an electronic amplification device, and signal processing circuitry through an optical fiber; wherein the signal processing circuitry detects the signal from each of the biosensors in the array.

In another aspect, a method of detecting a molecule in a solution places a biosensing system into contact with a solution containing the molecule; the biosensing system has a biocomponent that interacts with the molecule, and the biocomponent is in contact with a transducer that luminesces and whose luminescence is partially quenched with oxygen. The biosensing system also has a photon-detection device that has a fiber optical cable having a first end and a second end, the first end is in contact with a transducer and the second end is in contact with a signal processing system; and the signal processing system provides a concentration of the molecule in the solution. In one embodiment, the method of detecting a molecule in a solution uses a second end of the photon-detecting device that has an image sensor, and a signal processing system that has an avalanche photodiode coupled to a transimpedance amplifier whose output is coupled to a microprocessor whose output is coupled to a display that displays the concentration of the molecule in the solution.

In one aspect, a method of detecting a molecule in a solution places a biosensing system into contact with the solution containing the molecule. The biosensing system contains a biocomponent that interacts with the molecule, the biocomponent is in contact with a transducer that luminesces and whose luminescence is affected by hydrogen ions within the solution. The biosensing system also contains a photon-detection device that has a fiber optical cable having a first end and a second end, the first end is in contact with the transducer and the second end is in contact with a signal processing system; the signal processing system provides a concentration of the molecule in the solution. In one embodiment, the method of detecting the molecule in the solution uses a biosensing system that has a second end of the photon-detecting device having an image sensor and the signal processing system has an avalanche photodiode coupled to a transimpedance amplifier whose output is coupled to a microprocessor whose output is coupled to a display that displays the concentration of the molecule in the solution.

In one aspect, a method is disclosed of producing a biosensor distal tip having an ion sensing transducer and a biocomponent for use in detecting an analyte of a halogenated organic compound in an environment; the method has the steps of immobilizing the biocomponent which has at least one enzyme selected from hydrolases, subclass EC 3.8; and lyases, subclass EC 4.5, for carrying out a dehalogenation of the compound, to a surface of the tip by means selected from entrapping the at least one enzyme within a hydrogel secured to the surface; entrapping the at least one enzyme within a polymeric network secured to the surface; microencapsulating the at least one enzyme; covalent-bonding a second component of the biocomponent to the surface; cross-linking the at least one enzyme to a support material secured to the surface; and adsorbing the at least one enzyme into the surface; the method further involves treating the biocomponent for maintaining a period of enzymatic efficacy; and stabilizing the biocomponent by means selected from crosslinking a polymer layer to the biocomponent, adding a gel-hardening agent to the biocomponent, adding a stabilizing agent to the biocomponent, and modifying a component of the immobilizing means. In one embodiment, the method uses a step of immobilizing that further immobilizes a whole cell carrying the at least one enzyme, and the step of treating the biocomponent is selected from applying an inhibitor of protein synthesis to the biocomponent, adding a protease inhibitor to the biocomponent, freeze drying the biocomponent, and dry heating the biocomponent.

In one aspect, a method of producing a biosensor distal tip uses an ion sensing transducer and a biocomponent for use in detecting a halogenated analyte selected from s-triazine compounds, gamma-hexachlorocyclohexane, and DDT (1,1,1-trichloro-2,2-bis(p-chlorophenyl)ethane) in an environment; the method further uses the steps of: immobilizing the biocomponent which is a dehalogenase for carrying out a dehalogenation of the analyte, to a surface of the tip by means selected from entrapping the dehalogenase within a hydrogel secured to the surface; entrapping the dehalogenase within a polymeric network secured to the surface; microencapsulating the dehalogenase; covalent-bonding a second component of the biocomponent to the surface; cross-linking the dehalogenase to a support material secured to the surface; and adsorbing the dehalogenase into the surface; and stabilizing the biocomponent by means selected from crosslinking a polymer layer to the biocomponent, adding a gel-hardening agent to the biocomponent, adding a stabilizing agent to the biocomponent, and modifying a component of the immobilizing means. In one embodiment, a method of producing a biosensor distal tip uses an ion sensing transducer and a biocomponent for use in detecting an analyte such as a halogenated organic compound, the method uses the steps of immobilizing the biocomponent that is a dehalogenase for carrying out a dehalogenation of the compound, to a surface of the tip by entrapping the dehalogenase within a hydrogel secured to the surface; the ion-sensing transducer having been selected from the group consisting of a pH optode, a pH electrode, a field-effect transistor (FET), and an halide ion-selective electrode (ISE); the method further treats the biocomponent by means selected from applying an inhibitor of protein synthesis to the biocomponent, the protein synthesis inhibitor is selected from antibiotics such as chloramphenicol, aminoglycosides, tetracyclines, and macrolides; adding a protease inhibitor to the biocomponent; freeze drying the biocomponent, and dry heating the biocomponent; and crosslinking a polymer layer to the biocomponent.

DETAILED DESCRIPTION

Figure 1:
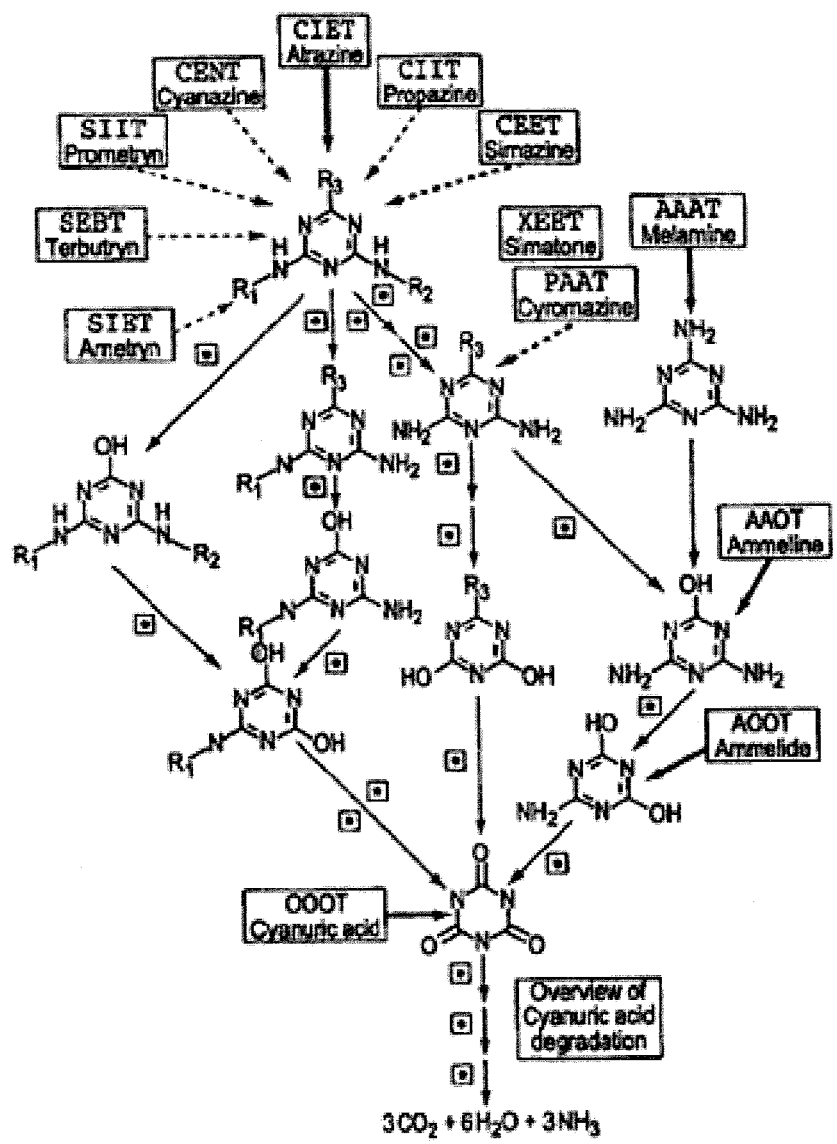
FIG. 1 is a depiction of several pathways of the degradation of an atrazine.

Biosensors have two key components: a biocomponent capable of sensing an analyte by producing some physical or chemical change in the analyte molecule; and a transducer, to which the biocomponent is immobilized, which converts this change into a measurable signal, whose magnitude is related to the concentration of the analyte of interest. The biocomponent preferably comprises a catalytic group such as an enzyme (whether utilized in purified form or in microorganisms and tissues). Enzymes are large, complex macromolecules, consisting largely of protein and usually containing a prosthetic group. As is well known, enzymes have catalytic activity, are highly specific to a particular substrate and are fairly fast acting. Typically the biosensor transducer is used to detect certain targeted by-products of the enzymatic reaction such as oxygen, ammonia, hydrochloric acid and carbon dioxide.

In spite of the many advantages of using an enzyme in a biocomponent, enzymes are quite sensitive to changes in pH, temperature, ionic strength, microorganisms and other biochemical factors in the microenvironments in which the biosensor is used. As a result, the enzyme(s) of a biocomponent can deactivate rapidly. Living cells contain at least a small amount of proteases which can, and do, degrade the intracellular proteins. Although pure enzymes are not exposed to potentially deactivating causes within a living cell of a microorganism, such as growth of unwanted proteases, there are tradeoffs: processes like extraction, isolation and purification of a particular enzyme from a complex cell environment can be expensive, tedious and complicated, as well as cause the enzyme to lose a high percentage of its activity.

Microorganisms are less expensive sources of enzymes than are purified enzymes and can aid in lowering the cost of biosensor production. The natural chemical composition of cells (whether recombinant or naturally produced) provides a useful environment for optimizing enzyme activity. However, living cells do require to a certain extent proper control of environment, maintenance and storage to retain their efficacy. Cell-based biosensors may have a longer response time and less specificity to a single analyte of interest due to the presence of other enzymes in the cells. Two known examples of cell-based sensors: a glucose sensor has been made using *Pseudomonas fluorescens* immobilized on an oxygen electrode; and another uses *Rhodococcus* sp. DSM 6344, is used to detect halogenated hydrocarbons. Like microorganisms, plant and animal tissues are enzyme-containing material that can be used to make cell-based biosensors. Antibodies are proteins that can bind with an antigen.

The nature of the interaction of the biological element with the analyte of interest impacts the choice of transduction technology. Transduction techniques can be categorized as follows:

Amperometric Electrode (an Electrochemical Transducer)

A constant potential is maintained on the working electrode with respect to a reference electrode, and the current generated by the oxidation or reduction of an electroactive species at the surface of the working electrode is measured; the response is linear. The reference electrode need not be drift-free to have a stable response. Since the signal generated is highly dependent on the mass transfer of the electroactive species to the electrode surface, there can be a loss in sensitivity due to fouling by species that adsorb to the electrode surface. Enzymes, particularly oxidoreductases, are well suited to amperometric transduction as their catalytic activity is concerned with electron transfer. Electroactive species that can be monitored at the electrode surface include substrates of a biological reaction (e.g., $O_2$, NADH), final products (e.g., hydrogen peroxide for oxidase reactions, benzoquinone for phenol oxidation) and also electrochemical mediators that can directly transfer electrons from the enzyme to a working electrode surface (e.g. hexacyanoferrate, ferrocene, methylene blue).

Potentiometric Electrode (an Electrochemical Transducer)

The potential difference between an active and a reference electrode is measured under the zero current flow condition. The three most commonly used potentiometric devices are ion-selective electrodes (ISEs), gas-sensing electrodes, and field-effect transistors (FETs). All these devices obey a logarithmic relationship between the potential difference and the activity of the ion of interest, thus, potentiometric electrode sensors have a wide dynamic range. One disadvantage of this transducer is the requirement of an extremely stable reference electrode. Ion-selective electrodes are commonly used to monitor aqueous environments (groundwater, waste water, etc.) FETs are commercially attractive as they can be used to build micro-biosensors according to currently available, widely used micro-electronic device production techniques.

Conductimetric Electrode (an Electrochemical Transducer)

These electrodes are used to measure salinity of marine environments. In this technique, conductance is measured by the application of an alternating current between two noble-metal electrodes immersed in the solution. Due to specific enzyme reactions, they convert neutral substrates into charged products, causing a change in the conductance.

Optical Transducers

Several types of photometric behavior are utilized by various opto-biosensors: ultraviolet-visible absorption, fluorescence (and phosphorescence) emission, bioluminescence, chemiluminescence, internal reflection spectroscopy (evanescent wave technology) and laser light scattering methods. When fluorescent reagents are utilized, a fluorescent substance is excited by incident light and as a result it emits light of longer wavelength. The intensity of emitted light changes when analyte binds with the fluorescent substance. The change in intensity can be measured as a response to a particular analyte. Suitable fluorescent reagents include trisodium 8-hydroxy-1,3,6-trisulphonate for pH sensors, fluoro (8-anilino-1-naphthalene sulphonate) for $Na^+$ ion sensor, and acridinium- and quinidinium-based reagents for halides. Chemiluminescence occurs by the oxidation of certain substances, usually with oxygen or hydrogen peroxide, to produce visible light. Bioluminescence is produced by certain biological substances, such as luciferins produced by firefly. Internal reflectance is a method based on the principle of total internal reflection of a light beam into an optically dense medium when the incident angle is greater than the critical angle. When such a process occurs, not all of the energy is confined in the optically dense medium. The internally reflected light generates an electromagnetic evanescent wave, which penetrates the lower density medium at the point of reflection, for a distance comparable to the wavelength of light. Techniques falling within the category of "light scattering": quasi-elastic light-scattering spectroscopy, photon correlation spectroscopy, and laser doppler velocimetry.

It is critical that the biocomponent be properly bound to the transducer; biocomponent immobilization techniques include:

Adsorption

The enzyme may be adsorbed onto one or more surface, partially or in whole, of the biocomponent material. Examples of materials to which enzymes may be adsorbed include: ion-exchange resins, ceramics, glass, polyvinyl chloride, chitin, chitosan, alumina, charcoal, glassy carbon, clay, cellulose, kaolin, silica gel, and collagen. Adsorption has been classified as physical adsorption (physisorption) and chemical adsorption (chemisorption). Physisorption is usually weak and occurs via the formation of van der Waals bonds or hydrogen bonds between the substrate and the enzyme molecules. Chemisorption is much stronger and involves the formation of covalent bonds.

(Micro)Encapsulation

A thin microporous semipermeable membrane is used to surround the biocomponent. Because of the proximity between the biocomponent and the transducer and the very small membrane thickness, biosensor response can be maximized. Suitable materials for (micro)encapsulation include nylon and cellulose nitrate. Further bonding of the biocomponent to the transducer surface may be done using a conductive polymer (polypyrrole). The membrane may be selected for its ability to serve additional functions, such as selective ion permeability, enhanced electrochemical conductivity or mediation of electron transfer. Membrane types used for microencapsulation include: cellulose acetate, polycarbonate, collage, acrylate copolymers, poly(ethylene glycol) polytetrafluroethylene (PTFE), agarose, as well as alginate-polylysine-alginate microcapsule formed of alginate and polylysine.

Entrapment

Cells or the pure enzymes are physically constrained (entrapped) to stay inside a three-dimensional matrix. Suitable materials (both natural and synthetic) for entrapment include those that permit uniform cell distribution and have biocompatibility and good transport mechanisms, such materials include without limitation, alginate, agarose and collagen. One might also choose to utilize mild polymerization techniques for more-rugged immobilization. Hydrogels are preferably used as an agent for biosensor entrapment; they provide a hydrophilic environment for the biocomponent and they require only mild conditions to polymerize. Hydrogels can absorb large quantities of water, which can facilitate desirable reactions such as hydrolysis. Both natural and synthetic hydrogels are suitable for use. The naturally occurring algal polysaccharides (such as agar, agarose, alginate, and carrageenan) and synthetic polymers such as polyacrylamide, polystyrene and polyurethane, are examples of such suitable hydrogels. Synthetic polymers generally have a smaller pore size which can lead to less leakage of biocomponent, and hence longer stability; however, synthetics are generally toxic and the immobilization process is accompanied by generation of heat and production of free radicals. Natural polymers are generally non-toxic and biodegradable, and the immobilization process is less stressful to the biocomponent. On the down side, natural polymers may provide less mechanical strength and stability, and their larger pore size allows predation by protozoans and other soil or water dwelling predators, as well as degradation by hydrolase enzymes in the environment being tested.

Alginate, a hydrogel, provides a good, biocompatible microenvironment for the biocomponent with gentle encapsulation process. It is a naturally occurring linear polymer composed of β-(1,4) linked D-mannuronic acid and α-(1,4)-L-guluronic acid monomers. Commercially, alginate is obtained from kelp, but bacteria such as *Azotobacter vinelandii*, several *Pseudomonas* species and various algae also produce it. When alginate is exposed to $Ca^{+2}$ ions, a cross-linking network is formed by the bonding of $Ca^{+2}$ ions and polyguluronic portions of the polymer strand by a process known as ionic gelation. The gelation process is temperature-independent. Complete gelling time without cells may be as little as 30 minutes. Sol-gel technology has enabled extension of the entrapment principle to silicate networks that have some advantageous characteristics, such as require milder polymerization processes and matrices that exhibit good mass-transport and molecular-access properties, particularly for electrochemical and optical transduction modes.

Cross-Linking

Here, the biocomponent is chemically bonded to solid supports or to another supporting material such as a gel. Bifunctional agents such as glutaraldehyde, hexamethylene diisocyanate and 1,5-dinitro-2,4-difluorobenzene may be used to bind the biocomponent to the solid support. While there is less leaching of the biocomponent and the layer tends to exhibit a long-term stability under more strenuous experimental conditions, such as exposure to flowing samples, stirring, washing, etc., cross-linking causes damage to the enzyme and may limit diffusion of the analyte in operation. By way of example, a tyrosinase biosensor for polyphenols was made by pretreating the electrode by polymerizing pyrrole in 0.1 M tetraethylammonium sulfonate on the surface. The tyrosinase solution and glutaraldehyde were then repetitively and alternately coated on the surface to cross-link the enzyme to the polypyrrole surface.

Covalent Bonding

Here, a particular group present in the biocomponent, which is not involved in catalytic action, is attached to the support matrix (transducer or membrane) by covalent bond. The radicals that take part in this reaction are generally nucleophilic in nature (e.g., $—NH_2$, $—COOH$, $—OH$, $—SH$ and imidazole groups). In order to retain enzyme activity, the reaction should be performed under mild conditions. In order to protect the active site, the reaction is often carried out in the presence of a substrate. Materials suitable for covalent bonding include: Cellulose and cellulose derivatives; Silica; Glass; Dextran; Starch; Agarose; Porous silica; Chitin; Chitosan.

Lifetime

The active lifetime of a biosensor-its period of enzymatic efficacy—depends upon the type of biocomponent used. Sensor lifetime can vary from a few days to a few months. Generally, pure enzymes have the lowest stability while cell and tissue preparations have the longer lifetimes. There are three aspects of lifetime of a biosensor: (i) the active lifetime of the biosensor in use, (ii) the lifetime of biosensor in storage, and (iii) the lifetime of the biocomponent in storage prior to being immobilized.

Biosensors of the invention have a wide variety of applications: (A) Medical uses include disposable one-way sensors (assays) for routine blood, saliva and urine testing, and in vivo sensors for monitoring crucial parameters during surgery or in intensive care units. (B) Food and drink industry applications include contaminant detection, verification of product content (analyze glucose and sucrose concentrations), monitoring of raw material conversion and evaluation of product freshness. (C) Process control applications include monitoring pH, temperature and substrate and dissolved gas concentrations in various processes such as fermentation and microbial and cell growth. (D) Environmental monitoring applications include monitoring concentration and toxicity of contaminants (e.g., analytes such as heavy metals, pesticides, etc.) in surface and groundwater and in waste streams and in soils. (E) Defense and Security Industry applications include measuring the presence of chemical warfare agents such as nerve gases and mustard gas; detection of trace vapors, explosives and drugs.

TABLE 2A

Dehalogenating enzymes for use in biosensor of the invention.

| Enzyme name(s) | EC code | Known substrates (analytes) | Reference(s) |
| --- | --- | --- | --- |
| Enzyme subclass 3.8: hydrolases acting on halide bonds: | | | |
| alkyl-halide halidohydrolase (alkylhalidase, halogenase; haloalkane halidohydrolase; haloalkane dehalogenase) | 3.8.1.1 | Bromochloromethane | [1] |
| 2-haloacid halidohydrolase, (2-haloacid dehalogenase, 2-haloalkanoid acid halidohydrolase; 2-haloalkanoic acid dehalogenase; L-2-haloacid dehalogenase; DL-2-haloacid dehalogenase) | 3.8.1.2 | Acts on 2-haloacids of short chain lengths, C2 to C4 | [2] [3] |
| haloacetate halidohydrolase (haloacetate dehalogenase, monohaloacetate dehalogenase) | 3.8.1.3 | Fluoroacetate and other haloacetates | [4] [5] |
| L-thyroxine iodohydrolase (reducing) (thyroxine deiodinase, thyroxine 5-deiodinase; diiodothyronine 5'-deiodinase; iodothyronine outer ring monodeiodinase; iodothyronine 5'-deiodinase) | 3.8.1.4 | A group of enzymes, removing iodine atoms sequentially from thyroxine. | [6] [7] [8] |
| 1-haloalkane halidohydrolase (haloalkane dehalogenase, 1-chlorohexane halidohydrolase; 1-haloalkane dehalogenase) | 3.8.1.5 | Acts on a wide range of 1-haloalkanes, haloalcohols, haloalkenes and some haloaromatic compounds. | [9] [10] [11] |
| 4-chlorobenzoate chlorohydrolase (4-chlorobenzoate dehalogenase, halobenzoate dehalogenase) | 3.8.1.6 | 4-chlorobenzoate and other halogenated benzoates | [12] [13] |
| 4-chlorobenzoyl CoA chlorohydrolase (4-chlorobenzoyl-CoA dehalogenase) | 3.8.1.7 | Specific for dehalogenation at the 4-position. Can dehalogenate substrates bearing fluorine, chlorine, bromine and iodine in the 4-position. This enzyme is part of the bacterial 2, 4-dichlorobenzoate degradation pathway. | [14] 15] |
| atrazine chlorohydrolase | 3.8.1.8 | Atrazine, simazine, and other halogenated s-triazines | [16] [17] |
| s-triazine hydrolase | 3.8.1.— | | |
| dichloroacetate halidohydrolase | 3.8.1.— | | |
| DL-2-haloacid dehalogenase | 3.8.1.— | | |
| 1,3,4,6-tetrachloro-1,4-cyclohexadiene halidohydrolase | 3.8.1.— | | |
| cis-chloroacrylic acid dehalogenase | 3.8.1.— | | |
| trans-chloroacrylic acid dehalogenase | 3.8.1.— | | |
| Enzyme subclass 4.5: lyases acting on carbon-halide bonds: | | | |
| DDT-dehydrochlorinase (DDT-ase) | 4.5.1.1 | DDT (1,1,1-trichloro-2,2-bis (4-chlorophenyl)ethane) | [18] [19] [20] |
| 3-chloro-D-alanine chloride-lyase (deaminating) (3-chloro-D-alanine dehydrochlorinase, B-chloro-D-alanine dehydrochlorinase) | 4.5.1.2 | 3-chloro-D-alanine | [21] [22] |
| dichloromethane chloride-lyase (chloride-hydrolysing) (dichloromethane dehalogenase) | 4.5.1.3 | Dichloromethane, dibromoethane, bromochloromethane, diiodomethane | [23] |
| L-2-amino-4-chloropent-4-enoate chloride-lyase (deaminating) (L-2-amino-4-chloropent-4-enoate dehydrochlorinase, L-2-amino-4-chloro-4-pentenoate dehalogenase) | 4.5.1.4 | L-2-amino-4-chloropent-4-enoate | [24] |
| 3-chloro-L-alanine chloride-lyase (adding thioglycolate) (S-carboxymethylcysteine synthase, S-carboxymethyl-L-cysteine synthase) | 4.5.1.5 | 3-chloro-L-alanine | [25] |
| halohydrin hydrogen-halide-lyase | 4.5.1.— | | |
| halohydrin hydrogen-halide-lyase B | 4.5.1.— | | |
| DDD dehydrochlorinase | 4.5.1.— | | |
| DDMS dehydrochlorinase | 4.5.1.— | | |
| gamma-hexachlorocyclohexane dehydrochlorinase | 4.5.1.— | | |
| 5-chloro-1,2,4-trihydroxybenzene dechlorinase | 4.5.1.— | | |
| Tribromobisphenol lyase | 4.5.1.— | | |

TABLE 2B

References for TABLE 2A (ordered in sequence as listed above)

Enzyme subclass 3.8: hydrolases acting on halide bonds (References as [numbered]):

[1] Heppel, L. A. and Porterfield, V. T. Enzymatic dehalogenation of certain brominated and chlorinated compounds. *J. Biol. Chem.* 176 (1948) 763-769.
[2] Goldman, P., Milne, G. W. A. and Keister, D. B. Carbon-halogen bond cleavage. 3. Studies on bacterial halidohyrolases. *J. Biol. Chem.* 243 (1968) 428-434. [Medline UI: 68123008]
[3] Motosugi, M., Esaki, N. and Soda, K. Preparation and properties of 2-halo acid dehalogenase from *Pseudomonas putida*. *Agric. Biol. Chem.* 46 (1982) 837-838.
[4] Goldman, P. The enzymatic cleavage of the carbon-fluorine bond in fluoroacetate. *J. Biol. Chem.* 240 (1965) 3434-3438.
[5] Goldman, P. and Milne, G. W. A. Carbon-fluorine bond cleavage. II. Studies on the mechanism of the defluorination of fluoroacetate. *J. Biol. Chem.* 241 (1966) 5557-5559. [Medline UI: 67053221]
[6] Chopra, I. J. and Teco, G. N. C. Characteristics of inner ring (3 or 5) monodeiodination of 3,5-diiodothyronine in rat liver: evidence suggesting marked similarities of inner and outer ring deiodinases for iodothyronines. *Endocrinology* 110 (1982) 89-97. [Medline UI: 82095045]
[7] Goswami, A., Leonard, J. L. and Rosenberg, I. N. Inhibition by coumadin anticoagulants of enzymatic outer ring monodeiodination of iodothyronines. *Biochem. Biophys. Res. Commun.* 104 (1982) 1231-1238. [Medline UI: 82182305]
[8] Smallridge, R. C., Burman, K. D., Ward, K. E., Wartofsky, L., Dimond, R. C., Wright, F. D. and Lathan, K. R. 3',5'-Diiodothyronine to 3'-monoiodothyronine conversion in the fed and fasted rat: enzyme characteristics and evidence for two distinct 5'-deiodinases. *Endocrinology* 108 (1981) 2336-2345. [Medline UI: 81188610]
[9] Keuning, S., Janssen, D. B. and Witholt, B. Purification and characterization of hydrolytic haloalkane dehalogenase from *Xanthobacter autotrophicus* GJ10. *J. Bacteriol.* 163 (1985) 635-639. [Medline UI: 85261076]
[10] Scholtz, R., Leisinger, T., Suter, F. and Cook, A. M. Characterization of 1-chlorohexane halidohydrolase, a dehalogenase of wide substrate range from an *Arthrobacter* sp. *J. Bacteriol.* 169 (1987) 5016-5021. [Medline UI: 88032819]
[11] Yokota, T., Omori, T. and Kodama, T. Purification and properties of haloalkane dehalogenase from *Corynebacterium* sp. strain ml5-3. *J. Bacteriol.* 169 (1987) 4049-4054. [Medline UI: 87307981]
[12] Muller, R., Thiele, J., Klages, U. and Lingens, F. Incorporation of [180] water into 4-hydroxybenzoic acid in the reaction of 4-chlorobenzoate dehalogenase from *Pseudomonas* sp. CBS 3. *Biochem. Biophys. Res. Commun.* 124 (1984) 178-182. [Medline UI: 85046491]
[13] Heppel, L. A., Porterfield, V. T. Enzymatic dehalogenation of certain brominated and chlorinated compounds. *J. Biol. Chem.* 176 (1948) 763-
[14] Chang, K. H., Liang, P. H., Beck, W., Scholten, J. D., Dunaway-Mariano, D. Isolation and characterization of the three polypeptide components of 4-chlorobenzoate dehalogenase from *Pseudomonas* sp. strain CBS-3. *Biochemistry* 31 (1992) 5605-5610. [Medline UI: 92304935]
[15] Crooks, G. P., Copley, S. D. Purification and characterization of 4-chlorobenzoyl CoA dehalogenase from *Arthrobacter* sp. strain 4-CB1. *Biochemistry*, 33 (1994) 11645-11649. [Medline UI: 95001870]
[16] de Souza, M. L., Wackett, L. P., Boundy-Mills, K. L., Mandelbaum, R. T. and Sadowsky, M. J. Cloning, characterization, and expression of a gene region from *Pseudomonas* sp. strain ADP involved in the dechlorination of atrazine. *Appl. Environ. Microbiol.* 61 (1995) 3373-3378. [Medline UI: 96035669]
[17] de Souza, M. L., Sadowsky, M. J. and Wackett, L. P. Atrazine chlorohydrolase from *Pseudomonas* sp. strain ADP: gene sequence, enzyme purification, and protein characterization. *J. Bacteriol.* 178 (1996) 4894-4900. [Medline UI: 96326334]

Enzyme subclass 4.5: lyases acting on carbon-halide bonds (References as [numbered]):

[18] Lipke, H. and Kearns, C. W. DDT dechlorinase. I. Isolation, chemical properties, and spectrophotometric assay. *J. Biol. Chem.* 234 (1959) 2123-2128.
[19] Lipke, H. and Kearns, C. W. DDT dechlorinase. II. Substrate and cofactor specificity. *J. Biol. Chem.* 234 (1959) 2129-2132.
[20] Moorefield, H. H. Purification of DDT-dehydrochlorinase from resistant houseflies. *Contr. Boyce Thompson Inst.* 18 (1956) 303-310.

Enzyme subclass 3.8: hydrolases acting on halide bonds (References as [numbered]):

[21] Nagasawa, T., Ishii, T. and Yamada, H. Physiological comparison of D-cysteine desulfhydrase of *Escherichia coli* with 3-chloro-D-alanine dehydrochlorinase of *Pseudomonas putida* CR 1-1. *Arch. Microbiol.* 149 (1988) 413-416. [Medline UI: 88251237]
[22] Yamada, H., Nagasawa, T., Ohkishi, H., Kawakami, B. and Tani, Y. Synthesis of D-cysteine from 3-chloro-D-alanine and hydrogen sulfide by 3-chloro-D-alanine hydrogen chloride-lyase (deaminating) of *Pseudomonas putida*. *Biochem. Biophys. Res. Commun.* 100 (1981) 1104-1110. [Medline UI: 81281807]
[23] Kohler-Staub, D. and Leisinger, T. Dichloromethane dehalogenase of *Hyphomicrobium* sp. strain DM2. *J. Bacteriol.* 162 (1985) 676-681. [Medline UI: 85182487]
[24] Moriguchi, M., Hoshino, S. and Hatanaka, S.-I. Dehalogenation and deamination of 1-2-amino-4-chloro-4-pentenoic acid by *Proteus mirabilis*. *Agric. Biol. Chem.* 51 (1987) 3295.
[25] Kumagai, H., Suzuki, H., Shigematsu, H. and Tuchikura, T. S-Carboxymethylcysteine synthase from *Escherichia coli*. *Agric. Biol. Chem.* 53 (1989) 2481-2487.

Stabilization of an immobilized biocomponent is important, whether a biosensor is to be stored for a prolonged period of time before use, in order to maximize performance of the biosensor to sense a selected ion (halide or hydrogen) in an environment. As mentioned, although enzymes are very selective and preferred here, enzymes share the disadvantage of low stability. As is the case in immobilization, stabilization technique depends on the biocomponent and type of transducer employed; techniques for stabilizing the biocomponent include:

Molecular Modification

The stability of enzymes can be improved by changing certain amino acids in the protein sequence—such as by site-directed mutagenesis, grafting of polysaccharides (or short chains of sugar molecules) onto the protein molecules, and other methods involving chemical and carbohydrate modifications.

Cross-Linking, Covalent Bonding, Entrapment, Encapsulation—These techniques considered useful as immobilization methods, can be used as supplements to the immobilization technique selected to improve enzyme stability by, for example: reducing the protein's mobility and thereby reducing degradation of its three-dimensional structure; or preventing loss of biocomponent from its immobilized matrix such as, when used in connection with an entrapment immobilization, by the addition of a selected gel-hardening agent such as glutaraldehyde, polyethyleneimine, hexamethylenediamine and formaldehyde.

Freeze Drying (Lyophilization)

This can provide for long-term preservation of microorganisms and enzymes. It involves removal of water from frozen bacterial suspensions by sublimation under reduced pressure. This process is performed in the presence of cryoprotective agents, such as glycerol and DMSO, which reduce the damage caused during freezing. Dried cells can be kept for a long period at 4° C. if kept away from oxygen, moisture and light and can be rehydrated and restored to their previous state. Two types of useful freeze drying include centrifugal freeze-drying and pre-freezing. Microorganisms that are sensitive to freeze-drying can be dried using the liquid-drying method.

Heat Shock

This process involves heating vacuum-dried cells at a high temperature (~300° C.) for a very short time (~2-3 minutes). With the proper temperature and heating time selected for cell type, cells can be killed but retain a viable enzyme system. These dead cells can be kept for a long time away from moisture without any requirement of nutrients.

Addition of Carbohydrates and Polymers

Freeze-dried enzymes are often stabilized by the addition of stabilizers, such as polyalcohols and sugars like trehalose, maltose, lactose, sucrose, glucose and galactose. This stabilization is due to the interaction of the polyhydroxyl compound with water in the system. This effectively reduces interaction between protein and water and thereby strengthens the hydrophobic interactions of the protein molecule to its surroundings.

Freezing

The metabolic activities of a microorganism may be reduced by storing them at very low temperatures (−150° C. to −190° C.), achieved using liquid nitrogen.

Atrazine is one of the most commonly applied s-triazine herbicides (structure below):

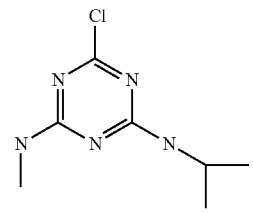

TABLE 3

Atrazine degradation pathway map identifies organisms that can initiate the pathways given.

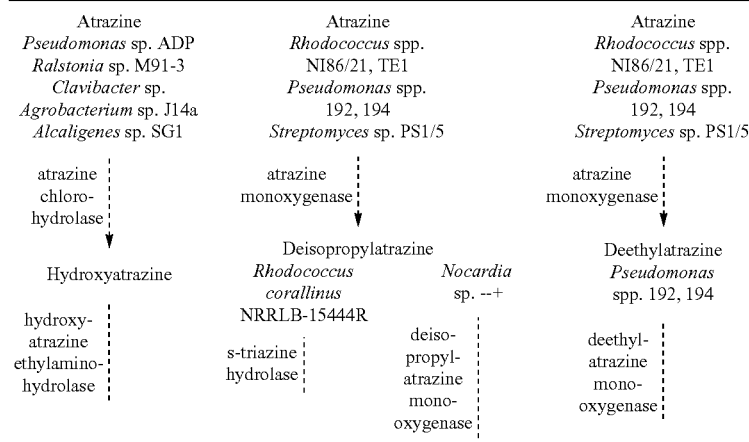

Figure 2:
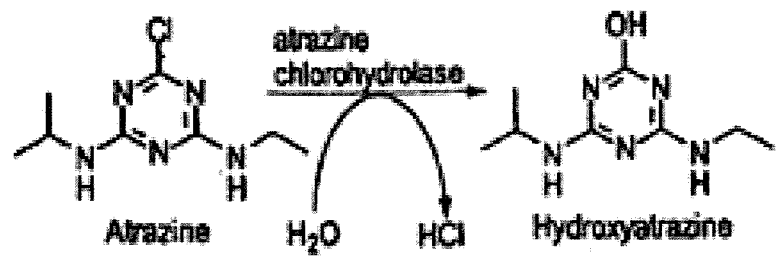
FIG. 2 depicts the hydrolytic dehalogenation of atrazine using atrazine chlorohydrolase.

FIG. 2 illustrates (see, also, left-hand column in above map) a hydrolytic dehalogenation of atrazine the first step of which can be carried out by several microorganism species, such as *Pseudomonas* sp. ADP, *Ralstonia* sp. M91-3, *Clavibacter* sp. ATZ1, *Agrobacterium* sp. J14a and *Alcaligenes* sp. SG1. The reaction depicted in the middle column in the above map represents an oxygenase attack on the isopropyl amino group; this reaction can be carried out by several microorganism species, such as *Rhodococcus* spp. N186/21 and TE1, *Pseudomonas* spp. 192 and 194 and *Streptomyces* sp. PS1/5. The reaction depicted in the right-hand column in the above map represents an oxygenase attack on the ethyl amino group; this reaction can be carried out by several species, such as *Rhodococcus* spp. N186/21 and TE1; *Pseudomonas* spp. 192 and 194 and *Streptomyces* sp. PS1/5.

Example 1

Figure 3:
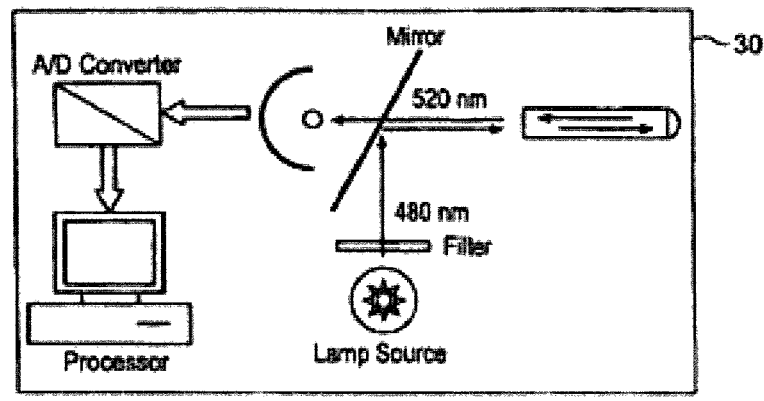
FIG. 3 schematically depicts an embodiment of a biosensing system.
Figure 4:
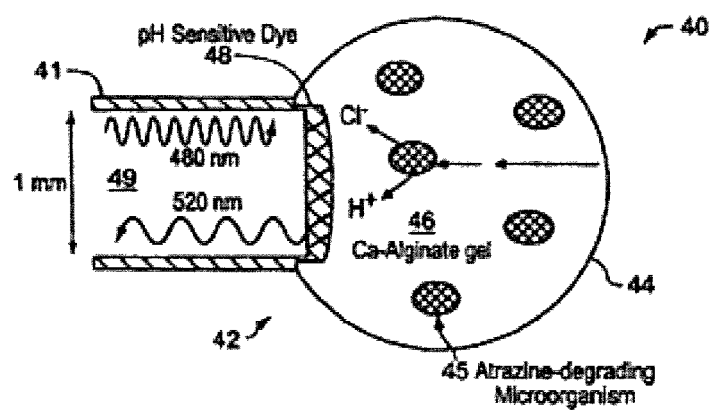
FIG. 4 depicts a biosensor distal tip utilizing a pH optode to which a dehalogenase has been immobilized by means of entrapment within a hydrogel matrix.

Biosensor employing pH optode with biocomponent, dehalogenase carried by whole cells immobilized by gel entrapment (for reference, see FIGS. 3 and 4). Distal tip section was coupled to a 1-m long polymethylmethacrylate (PMMA) fiber optic cable. Cells stored at 4° C. in phosphate-buffered saline were centrifuged at 15,000×g for 2 min.; the pellet was then washed twice with saline (9 g/L of NaCl [pH 7.1]) containing 50 μg/mL of chloramphenicol. Next, sodium-alginate (4% w/v in water) containing about 100 µg/mL of chloramphenicol was added and mixed well with the cell pellet. This cell-alginate mixture was kept for 5 minutes at room temperature before it was used to make the biosensor. The cell-alginate mixture was stirred well with a pipette tip and a small drop of gel was carefully deposited on the tip of the pH optode. The tip was dipped into an ice-cold solution of 7% (w/v) of $CaCl_2.2H_2O$ for 15 minutes. When exposed to $Ca^{+2}$ ions, a cross-linking network was formed by the bonding of $Ca^{+2}$ ions and polyguluronic portions of the polymer strand by a process known as ionic gelation. After immobilization, the tip was about 2 mm in diameter. A protease inhibitor cocktail in 1 mL of saline solution was prepared by adding 215 mg of lyophilized protease inhibitor in a solution containing 1 mL of DMSO (Dimethyl sulfoxide) and 4 mL of deionized water. The cocktail had a broad specificity for the inhibition of serine, cysteine, aspartic and metalloproteases, and aminopeptidases.

Example 2

The alginate bead was coated with poly-L-lysine (PLL). First, a biosensor was prepared with microorganism strain ADP. The Ca-alginate bead on the biosensor tip (nearly 1 mm) was washed twice with saline solution (9 g/L of NaCl in water). The biosensor tip was immersed in 10 mL of 0.4% (w/v) of poly-L-lysine. HCl solution in saline for 30 min. at 30° C. In order to remove unreacted PLL from the bead surface, tip was washed with saline solution.

Example 3

Two microorganisms suitable for use in degrading atrazine are *Pseudomonas* sp. strain ADP and *Clavibacter michiganese* ATZ1. Studies have shown that strain ADP has three genes (atz-A, atz-B and atz-C) that encode enzymes responsible for the degradation of atrazine to cyanuric acid. Strain ATZ1 has 100% homology only with atz-A; and thus only carries out reactions similar to the first two steps of strain ADP. For further reference, see tables below:

TABLE 8.1

Physical methods used to design a biosensor

| | |
|---|---|
| PHYSICAL TRANSDUCER | Optical transduction; fluorescent dye |
| IMMOBILIZATION METHOD | Entrapment: Ca-alginate gel matrix, time of gelation = 20 minutes |
| BIOCOMPONENT | Whole cell of atrazine degrading strain: treated under various conditions |
| STABILIZATION METHOD | Storage in refrigerator at 4° C. |
| SIZE | Less than 2 mm diameter of immobilized gel: cell density ~1 g of wet wt. of cells/wt. of alginate |

TABLE 8.2

Summary of sensitivity parameters for the biosensor

| Microorganism used as a biocomponent | Linear Range (ppb) | Detection Limit | Response Time (90% of response for change of 25 ppb of atrazine conc., ~2 mm bead dia.) | Reproducibility (standard deviation based on 3 measurements) |
|---|---|---|---|---|
| ADP | 0-125 | <1 ppb | 19.7 ± 2.5 | <6% |
| ATZI | 0-100 | <1 ppb | 10.7 ± 2.3 | <5% |

TABLE 8.4

Summary of results of activity retention of the biosensor using different types of biocomponents.

| Type of microorganism Used as biocomponent | Activity retention > 90% (days) | Activity retention > 30% (days) |
|---|---|---|
| ADP | 5 | 7 |
| Heat-treated ADP | 7 (dry heating time = 30 sec) | 11 |
| | 9 (dry heating time - 60 sec) | 12 |
| Chloramphenicol-treated ADP | 8 (Conc. of chloramphenicol = 50 µg/mL) | 9-10 |
| | 10 (Conc. of chloramphenicol = 200 µg/mL) | 60% activity retention on the $12^{th}$ day |
| Protease inhibitor-treated ADP | 6 | 10 |
| ATZ1 | 5 | 11 |

Once again, turning to the figures: FIG. 1 is a depiction of several pathways derived from general knowledge of the degradation of the s-triazine, atrazine. FIG. 2 depicts a hydrolytic dehalogenation of atrazine using atrazine chlorohydrolase. FIG. 3 schematically depicts features of a known system 30 suitable for use in connection with employing a pH optode as the transducer [Campbell, 1998]. This fiber optic pH sensor system 30 includes the pH optode with biocomponent, a lens focusing system, a photomultiplier (PMT), an A/D converter and suitable microprocessor. FIG. 4 schematically depicts features of the improved distal tip 42 of the invention, an embodiment utilizing a pH optode 49 to which biocomponent 44 comprising the dehalogenase 45 (either in pure form or carried in a microorganism at 45) has been immobilized by means of entrapment within a hydrogel or polymer matrix (at 46), as shown bulbous/enlarged for clarity. The pH optode 49 has suitable cladding 41 for purposes of protecting the fiber (s) of the optical element (single or bundle) therewithin. Information about the environment 40 (soil or aqueous, for example) can be collected according to the invention, all as disclosed hereby.

Figure 5:
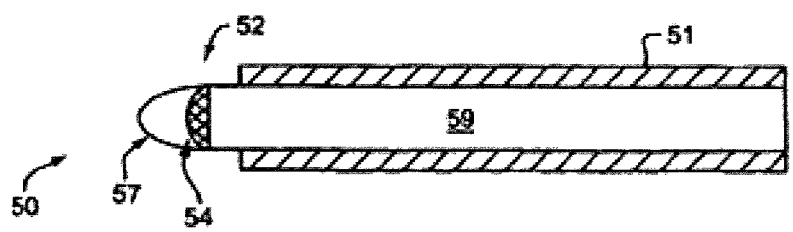
FIG. 5 schematically depicts the first end of a fiber optical cable having a transducer layer and a matrix layer containing a biocomponent.

FIG. 5 schematically depicts features of a distal tip 52 embodiment of the invention wherein two different matrices of a hydrogel or polymer are superimposed—the layer adjacent the distal tip 54 surface preferably having a higher concentration of dehalogenase (whether carried by whole cells or in pure form) than the outermost layer 57. The pH optode 59 has suitable cladding 51 for purposes of protecting the fiber (s) of the optical element (single or bundle) therewithin. Information about the environment 50 (soil or aqueous, for example) can be collected according to the invention, all as disclosed hereby.

Figure 6:
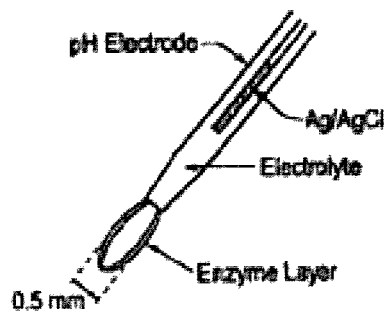
FIG. 6 schematically depicts features of a biosensor using a pH electrode.
Figure 7:
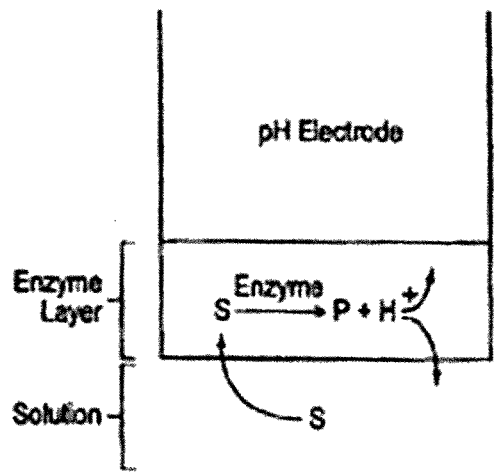
FIG. 7 schematically depicts further details of the pH electrode depicted in FIG. 6.
Figure 8:
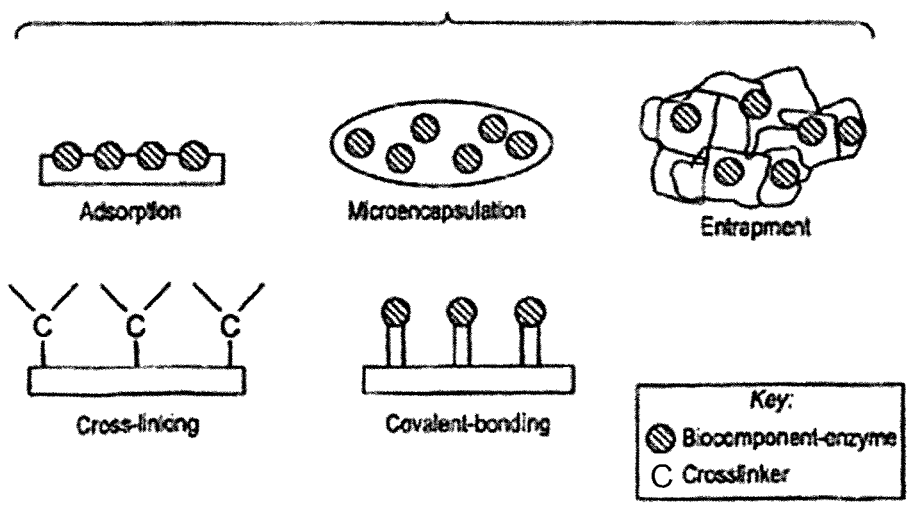
FIG. 8 schematically depicts several techniques for immobilizing the biocomponent.
Figure 9:
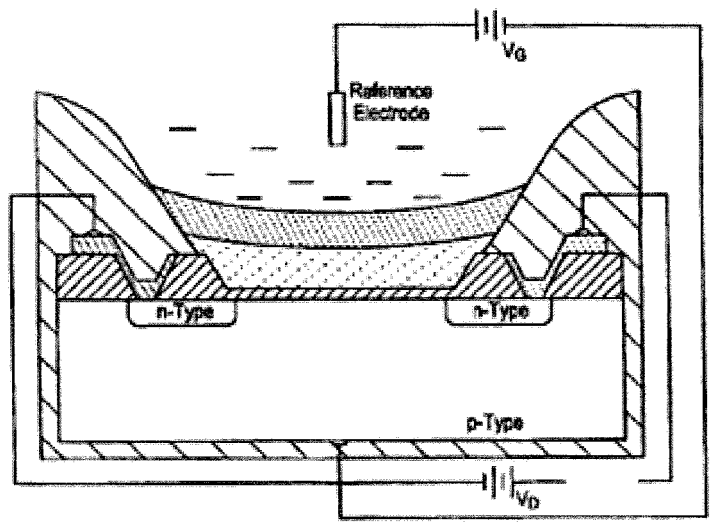
FIG. 9 schematically depicts features of a micro-sized biosensor where the transducer employed is a Field Effect Transistor (FET)-type to which a biocomponent is immobilized.
Figure 10:
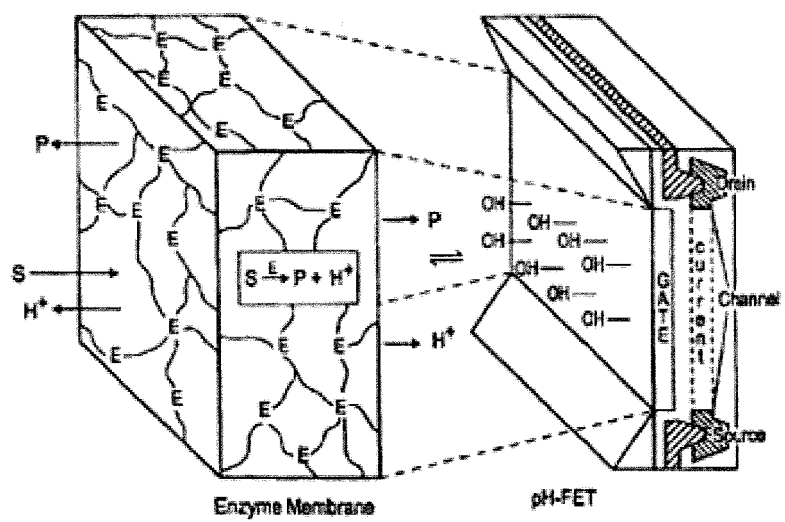
FIG. 10 schematically depicts further details of the pH-sensitive FET transducer depicted in FIG. 9.

FIG. 6 schematically depicts features of a distal tip embodiment of the invention employing a pH microelectrode transducer, an enzyme-containing biocomponent immobilized to the distal tip. FIG. 7 schematically represents further details of the pH electrode depicted in FIG. 6, featuring the reaction within the enzymatic layer of the analyte of interest (here, S, for 'substrate') in general terms—the diffusion of S resulting in products P and $H^+$—as is well known. FIG. 8 schematically represents several immobilization techniques as identified according to the invention. FIG. 9 schematically depicts features of a micro-sized embodiment of the invention wherein the transducer employed is a Field Effect Transistor (FET) type to which a biocomponent is immobilized. FIG. 10 schematically represents further details of the pH-sensitive FET transducer depicted in FIG. 9, featuring the reaction within the enzymatic layer of the analyte of interest (here, S, for 'substrate') in general terms—the diffusion of S resulting in products P and $H^+$—as is well known.

As one can appreciate, feature details for a method to produce a distal tip of the invention are readily ascertainable by reviewing the accompanying figures and supporting text such that further visual depiction is unnecessary.

While certain representative embodiments and details have been shown merely for the purpose of illustrating the invention, those skilled in the art will readily appreciate that various modifications may be made to these representative embodiments without departing from the novel teachings or scope of this invention. Accordingly, all such modifications are intended to be included within the scope of this invention as defined in any illustrative-claim included below. Although the commonly employed preamble phrase "comprising the steps of" may be used herein, or hereafter, in a method claim, the Applicants in no way intend to invoke 35 U. S. C. Section 112 §6. Furthermore, in any claim that is filed hereafter (as well as any claim included herewith for illustrative purposes), any means-plus-function clauses used, or later found to be present, are intended to cover the structures described herein as performing the recited function and not only structural equivalents but also equivalent structures.

What is claimed is:

1. A biosensor for measuring the concentration of a molecule in a solution comprising:
    a fiber optical cable having a first end and a second end, and
    a transducer layer comprising an optical transducer capable of interacting with oxygen, protons, or halide ions, the transducer layer having a first side and a second side, and
    a matrix layer comprising a hydrogel or polymer matrix having a first side and a second side, and
    a biocomponent immobilized within said matrix layer,
    wherein said first end of said fiber optical cable is bound to said second side of said transducer layer, and
    wherein said first side of said transducer layer is bound to said second side of said matrix layer, and
    wherein said first side of said matrix layer is in contact with said solution, and
    wherein said second end of said fiber optical cable is coupled to an optical excitation source, a photon detection device, an electronic amplification device, signal processing circuitry and a signal output device.

2. The biosensor of claim 1 wherein said transducer layer comprises an optical transducer selected from the group consisting of:
    an ultraviolet-visible absorption transducer,
    a luminescence transducer selected from the group consisting of trisodium 8-hydroxy-1,3,6-trisulphonate, fluoro (8-anilino-1-naphthalene sulphonate), tris(bipyridine)ruthenium(II) complex, ruthenium complexes, and acridinium- and quinidinium-based reagents,
    a fluorescence transducer,
    a phosphorescence transducer,
    an emission transducer,
    a bioluminescence transducer,
    a chemiluminescence transducer, an internal reflection spectroscopy transducer, and
    a laser light scattering methods transducer selected from the group consisting of quasielastic light-scattering spectroscopy, photon correlation spectroscopy and laser Doppler velocimetry.

3. The biosensor of claim 1 wherein said polymer matrix in said matrix layer comprises one or more of polyacrylamide, polystyrene, polymethacrylate, polyvinylalcohol and polyurethane.

4. The biosensor of claim 1 wherein said hydrogel in said matrix layer comprises one or more of algal polysaccharides, agarose, alginate, gelatin, collagen, pectin, poly(carbamoyl) sulfonate, locust bean gum, and gellan.

5. The biosensor of claim 1 wherein said biocomponent is treated to stabilize said biocomponent against degradation using one or more methods comprising:
    adding inhibitors of protein synthesis to said biocomponent,
    adding protease inhibitors to said biocomponent,
    freeze drying said biocomponent,
    dry heating said biocomponent, and
    grafting a molecule onto said biocomponent, said molecule one or more of polysaccharides, polyalcohols, trehalose, maltose, lactose, sucrose, glucose and galactose.

6. The biosensor of claim 1 wherein said first end of said fiber optical cable is coated with one or more agents comprising one or more of cellulose acetate, polycarbonate, collagen, acrylate copolymers, poly(ethylene glycol), polytetrafluoroethylene, and alginate-polylysine-alginate microcapsules.

7. The biosensor of claim 1 wherein said biocomponent is treated through adding one or more gel-hardening agents to said biocomponent immobilized within said matrix layer.

8. The biosensor of claim 1 wherein said transducer layer is covalently bound to one or more agents bound to the first end of said fiber optical cable, said one or more agents comprising one or more of cellulose, cellulose derivatives, silica, glass, dextran, starch, agarose, porous silica, chitin and chitosan.

9. The biosensor of claim 7 wherein said one or more gel-hardening agents comprise one or more of glutaraldehyde, polyethyleneimine, hexamethylenediamine, hexamethylene diisocyanate, 1,5-dinitro-2,4-difluorobenzene and formaldehyde.

10. The biosensor of claim 1 comprising a capillary tube having a first end and second end, wherein said second end of said capillary tube is coupled to a source of a molecule, said molecule is selected from the group consisting of oxygen, hydrogen peroxide, NADH, NADPH, a cofactor, or a substrate of said biocomponent, and
    wherein said first end of said capillary tube is coupled to said matrix layer, and wherein said molecule is delivered into said matrix layer through said capillary tube.

11. The biosensor of claim 1 wherein said optical excitation source is selected from the group consisting of a halogen lamp, laser, and light emitting diode.

12. The biosensor of claim 1 wherein said electronic amplification device comprises a photomultiplier tube, an avalanche photodiode, and a p-i-n photodiode having an integrated amplifier.

13. The biosensor of claim 1 wherein said biocomponent is an enzyme.

14. The biosensor of claim 13 wherein a nucleotide coding sequence of said enzyme is part of a plasmid within a whole cell or is part of a chromosome of a whole cell and wherein said whole cell is within said matrix layer.

15. The biosensor of claim 1 wherein said biocomponent is selected from the group consisting of purified enzymes, live whole cells, and dead whole cells.

16. The biosensor of claim 1 arranged as an array of biosensors wherein each biosensor comprises a different biocomponent or mixture of biocomponents,
   wherein each of said biocomponent interacts with one type of transducer.

17. The biosensor of claim 1 arranged as an array of biosensors wherein each biosensor comprises a different biocomponent or mixture of biocomponents, wherein said molecule is an analyte and said solution comprises a group of analytes, and wherein each biocomponent has a different substrate specificity for each analyte among said group of analytes, and wherein said difference in substrate specificity of each of said biocomponents in said array is used to determine individual concentrations of each analyte among said group of analytes.

18. The biosensor of claim 16 wherein each of said biosensors in said array are individually coupled to an optical excitation source, a photon detection device, an electronic amplification device, and signal processing circuitry through an optical fiber and wherein said signal processing circuitry detects the signal from each of said biosensors in said array.

19. The biosensor of claim 16 wherein each of said biosensors in said array are coupled to an optical excitation source, a photon detection device, an electronic amplification device, and signal processing circuitry through an optical fiber and wherein said signal processing circuitry detects the signal from each of said biosensors in said array.

* * * * *